US010688163B2

(12) United States Patent
Jackson et al.

(10) Patent No.: US 10,688,163 B2
(45) Date of Patent: Jun. 23, 2020

(54) TARGETED ANTIMICROBIALS AND RELATED COMPOSITIONS, METHODS AND SYSTEMS

(71) Applicant: LAWRENCE LIVERMORE NATIONAL SECURITY, LLC, Livermore, CA (US)

(72) Inventors: Paul J. Jackson, Livermore, CA (US); Brian E. Souza, Livermore, CA (US); Feliza A. Bourguet, Livermore, CA (US); Matthew A. Coleman, Oakland, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 0 days.

(21) Appl. No.: 14/457,035

(22) Filed: Aug. 11, 2014

(65) Prior Publication Data

US 2014/0369990 A1 Dec. 18, 2014

Related U.S. Application Data

(63) Continuation of application No. 12/852,358, filed on Aug. 6, 2010, now Pat. No. 8,821,860.

(60) Provisional application No. 61/232,345, filed on Aug. 7, 2009.

(51) Int. Cl.
| | |
|---|---|
| *C07K 14/195* | (2006.01) |
| *A61K 38/50* | (2006.01) |
| *C12Q 1/18* | (2006.01) |
| *C12P 1/04* | (2006.01) |
| *A61K 45/06* | (2006.01) |

(52) U.S. Cl.
CPC .............. *A61K 38/50* (2013.01); *A61K 45/06* (2013.01); *C12P 1/04* (2013.01); *C12Q 1/18* (2013.01); *C12Y 305/01028* (2013.01); *G01N 2333/32* (2013.01); *G01N 2333/914* (2013.01)

(58) Field of Classification Search
CPC .......... C07K 14/195; C12Y 302/01017; A01N 63/00

See application file for complete search history.

(56) References Cited

U.S. PATENT DOCUMENTS 8,389,469 B2 3/2013 Yoong et al.

OTHER PUBLICATIONS

Yoong amino acid sequence alignment, 2016.*

Porter, C.J. et al. *The 1.6 Å Crystal Structure of the Catalytic Domain of PlyB, a Bacteriophage Lysin Active Against Bacillus anthracis*.J. Mol. Biol., vol. 366, 2007, pp. 540-550.

S.M. Kelly et al. "The Use of Circular Dichroism in the Investigation of Protein Structure and Function" Current Protein and Peptide Science, 2000, vol. 1, No. 4, pp. 349-384.

Bourguet et al., "Characterization of a novel lytic protein encoded by the *Bacillus cereus*E33L gene ampD as a *Bacillus anthracis* antimicrobial protein", *Applied and Environmental Microbiology*, Apr. 2012, vol. 78, No. 8, p. 3025-3027.

De Boer, et al., "Cell Wall Turnover in Growing and Nongrowing Cultures of *Bacillus subtilis", Journal of Bacteriology*, vol. 149 (3), p. 977-984, 8 pages, Mar. 1982.

Herbold, et al., "*Bacillus subtilis* N-Acetylmuramic Acid L-Alanine Amidase", *The Journal of Biological Chemistry*, vol. 250 (5), 1676-1682, (1975), 8 pages.

Herbold, et al., "Interaction of N-Acetylmuramic Acid L-Alanine Amidase with Cell Wall Polymers", *The Journal of Biological Chemistry*, vol. 250 (18), 7231-7238, 9 pages, 1975.

Jolliffe, et al., "Extracellular Proteases Modify Cell Wall Turnover in *Bacillus subtilis", Journal of Bacteriology*, vol. 141 (3), 1199-1208, 10 pages, Mar. 1980.

* cited by examiner

*Primary Examiner* — Karen Cochrane Carlson
(74) *Attorney, Agent, or Firm* — Steinfl + Bruno

(57) ABSTRACT

Targeted antimicrobials are described and related, compositions, methods and systems.

40 Claims, 7 Drawing Sheets

Specification includes a Sequence Listing.

FIG. 7 ic # TARGETED ANTIMICROBIALS AND RELATED COMPOSITIONS, METHODS AND SYSTEMS

CROSS REFERENCE TO RELATED APPLICATIONS

This application is a U.S. Continuation Application of U.S. patent application Ser. No. 12/852,358 entitled "TARGETED ANTIMICROBIALS AND RELATED COMPOSITIONS, METHODS AND SYSTEMS," filed on Aug. 6, 2010, which, in turn, claims priority to U.S. Provisional Application entitled "Targeted Antimicrobials Based on Recombinant Muramidases" Ser. No. 61/232,345, filed on Aug. 7, 20009, the disclosure of each of which is incorporated herein by reference in its entirety.

STATEMENT OF GOVERNMENT GRANT

The United States Government has rights in this invention pursuant to Contract No. DE-AC52-07NA27344 between the United States Department of Energy and Lawrence Livermore National Security, LLC, for the operation of Lawrence Livermore National Laboratory.

TECHNICAL FIELD

The present disclosure relates to targeted antimicrobials and related compositions, methods and systems.

BACKGROUND

Efforts to identify antimicrobial compounds that are highly specific for a particular bacterial pathogen are increasing due to various applications wherein specific targeting of bacteria is desired. In numerous fields and applications, such as emergence of targeted therapy, it is more rational to use antimicrobial agents that are specific for one or more bacteria. Moreover, as more bacterial pathogens become resistant to available antibiotics, new agents must be developed that cannot be circumvented, consumed or destroyed by the targeted pathogens.

Bacteriophages (phages) have long been considered potential antibacterial agents while bacteriophage endolysins, the small proteins responsible for lysis of the infected host cell, have been studied more recently.

SUMMARY

Provided herein, are targeted antimicrobials and related compositions, methods and systems, that in several embodiments, allow highly specific enzymatic and recognition activity to effectively destroy bacterial targets.

According to a first aspect, a method is described, to identify an antimicrobial specific for one or more related microorganisms (herein also indicated as targeted antimicrobial). The method comprises: identifying at least one lytic enzyme expressed by a microorganism or by a microorganism related thereto to provide a candidate antimicrobial. In the method the at least one lytic enzyme is capable of targeting one or more moieties presented on the exterior of the microorganism, the one or more moieties providing the microorganism with structural support and/or protection. The method further comprises contacting the candidate antimicrobial with the microorganism for a time and under condition to allow an antimicrobial activity of the candidate antimicrobial on the microorganism and selecting among the at least one candidate antimicrobial, a selected candidate antimicrobial having a detectable antimicrobial activity for the microorganism.

According to a second aspect a targeted antimicrobial is described that is expressed by a microorganism and is specific for the microorganism expressing the antimicrobial and/or for a microorganism related thereto. The antimicrobial is obtainable by methods to identify a targeted antimicrobial herein described.

According to a third aspect, an antimicrobial composition is described. The antimicrobial composition comprises one or more targeted antimicrobials herein described and a suitable vehicle. In some embodiments, the vehicle is a pharmaceutically acceptable vehicle and the composition is a pharmaceutical composition.

According to a fourth aspect, an antimicrobial method is described that is specific for one or more related microorganisms, the method comprising contacting the microorganism with a targeted antimicrobial herein described that is specific for the one or more microorganisms expressing. In the method, the contacting is performed in vitro or in vivo for a time and under condition to specifically kill or inhibit the growth of the one or more related microorganism. In some embodiments, wherein the contacting is performed in vivo, the contacting can be performed by administering the targeted antimicrobial to an individual in a therapeutically effective amount to treat or prevent a condition associated with the microorganism in the individual.

According to a fifth aspect, an antimicrobial method is described. The antimicrobial method comprises contacting a targeted antimicrobial specific for one or more related microorganisms with a medium suitable to host the one or more related microorganisms, for a time and under conditions to specifically kill or inhibit the growth of the one or more related microorganisms if present in the medium.

According to a sixth aspect, an antimicrobial system is described. The system comprises at least two components selected from: one or more targeted antimicrobials for one or more related microorganisms; suitable reagents and an additional antimicrobial, for simultaneous combined or sequential use in an antimicrobial method targeting the microorganism.

According to a seventh aspect a method for in vitro molecule production is described. The method comprises contacting a microorganism comprising a molecule of interest with a targeted antimicrobial herein described that is specific for the microorganism for a time and under condition to provide a lysed microorganism and extracting the molecule of interest from the lysed microorganism.

According to an eight aspect, an in vitro molecule production system is described. The system comprises at least two components selected from: one or more targeted antimicrobial for a microorganism herein described; suitable reagents and an additional antimicrobial, for simultaneous combined or sequential use in an in vitro molecule production method targeting the microorganism.

The targeted antimicrobials and related compositions, methods and systems herein described can be used in connection with applications wherein antimicrobial activity specific for one bacterium and/or a group of bacteria is desired, including but not limited to medical application, disinfection, biological analysis, and diagnostics including but not limited to clinical applications and applications directed to automated extraction of molecules from a microorganism, and additional applications identifiable by a skilled person.

The details of one or more embodiments of the disclosure are set forth in the accompanying drawings and the description below. Other features will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description and examples sections, serve to explain the principles and implementations of the disclosure.

Figure 1:
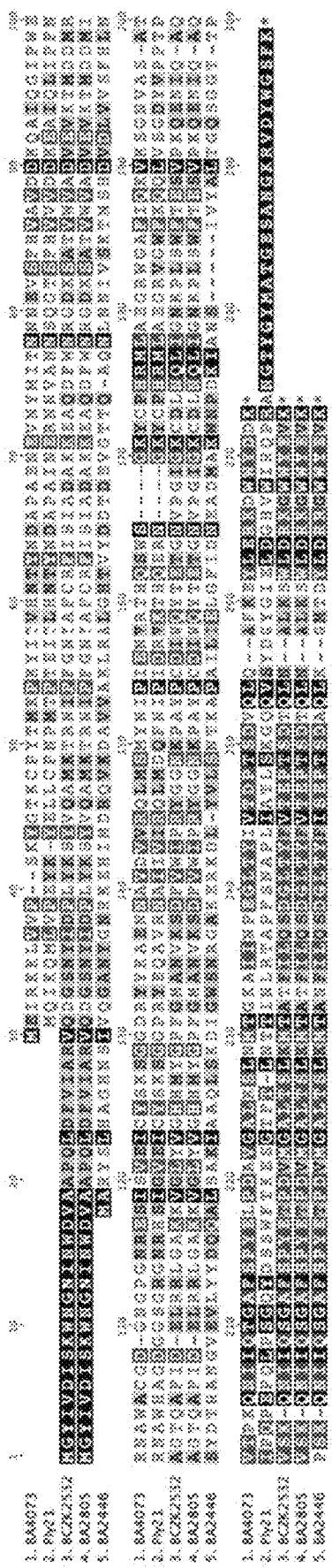
FIG. 1 shows an amino acid sequence alignments of lytic proteins encoded by genes from the *B. anthracis* and *B. cereus* E33L genomes and compared to the bacteriophage Ply21 amino acid sequence. Amino acid sequences of BA4073 (SEQ ID NO: 1), Ply21 (SEQ ID NO: 2), BCZK2532 (SEQ ID NO: 3), BA2805 (SEQ ID NO: 4) and BA2446 (SEQ ID NO: 5) were aligned using Geneious Pro 5.0.3 software. The bacteriophage endolysin sequence was included for comparison. Levels of homology are visualized with various shades of gray, wherein a darker shade indicates a greater homology and the highest homology is marked in black.

FIG. 2 shows a picture of a polyacrylamide gel illustrating the results of in vitro transcription-translation (IVT) results expressing four different *Bacillus* endolytic proteins. Lane 1 contains a molecular weight marker. Lanes 2 and 3 contain products from reactions containing two different plasmid clones of BCZK2195; lanes 4 and 5 contain products from reactions containing two different plasmid clones of BA2446; lanes 6 and 7 contain products from reactions containing two different plasmid clones of BCZK2532; lanes 8 and 9 contain products from reactions containing two different plasmid clones of BA2805. Lane 10 contains products from a reaction containing a cloned green fluorescent protein (GFP) sequence and Lane 11 contains products from a no-DNA control reaction.

FIG. 3 shows SDS-PAGE gels illustrating the results of in vitro synthesis and purification of BCZK2532 endolysin. FIG. 3*a* shows a Coomassie Blue stained SDS-PAGE gel analysis of an IVT synthesis. Lane 1, molecular weight marker; lanes 2, 3 and 4, total proteins from IVT reactions containing the pIVEX2.4d/BCZK2532 plasmid DNA; lane 5; results of flow-through upon loading a reaction on a Nickel-affinity column to purify the endolysin from other IVT components; lane 6, 0 mM imidazole wash 1; lane 7, 0 imidazole wash 2. FIG. 3*b* shows purification of the BCZK2532 from the Nickel-affinity column. Lane 1, molecular weight marker, lanes 2 through 5, 4 successive 10 mM imidazole washes; lanes 6 through 8, elution of purified endolysin from the column. FIG. 3*c*, purified BCZK2532 and Ply21 endolysins. Lane 1, molecular weight marker; lane 2, purified BCZK2532 endolysin; lane 3, purified Ply21 endolysin.

FIG. 4 shows a picture of a Petri dish illustrating the results of *Bacillus* lytic protein spot tests. Each spot is labeled with the protein deposited on that spot as identified in the examples section of the present disclosure. Ten μl of IVT synthesized green fluorescent protein (GFP) was spotted on the plate as a negative control and 10 μl of bacteriophage LAB80, a bacteriophage that infects *B. anthracis*, was spotted as a positive control. Equal amounts of each lytic protein were spotted on the plates. Ply21 protein was also included in the study for comparison.

FIG. 5 shows diagrams illustrating the results of lysis of *B. anthracis* Sterne cells expressing the Green Fluorescent Protein (GFP) with BCZK2532. FIG. 5*a* shows flow cytometric analysis of *B. anthracis* cells exposed for different times to the endolysin. -○-, no endolysin; -■-, 1 nM endolysin; -●-, 10 nM endolysin; -▲-, 50 nM endolysin; -◆-, 100 nM endolysin. FIG. 5*b* shows the percent survival of *B. anthracis* cells based on the number of colony forming units (CFU) that remain after treatment BCZK2532 endolysin. -○-, no endolysin; -■-, 1 nM endolysin; -●-, 10 nM endolysin; -▲-, 50 nM endolysin; -◆-, 100 nM endolysin.

FIG. 6 shows images of a microscopic visualization of BCZK2532 endolysin treatment. FIG. 6A shows a micrograph of *B. anthracis* Sterne cells after exposure to 2.5 μg/mL for 0 minutes. FIG. 6B show a micrograph of *B. anthracis* Sterne cells after exposure to 2.5 μg/mL for 3 minutes. Both images, frames taken from a movie of cell lysis, are of the same microscopic field before and after treatment with the endolysin.

FIG. 7 shows a diagram illustrating results of treatment of six different *Bacillus* isolates according to an embodiment herein described. Results shown are from two different plating experiments. Results are plotted as percent survival compared to untreated cells. Black bars show results of cells treated with BCZK2532 endolysin. Gray bars show results of cells treated with Ply21 endolysin. Starting concentrations of the two enzymes were the same.

DETAILED DESCRIPTION

Provided herein are a method to identify targeted antimicrobials and related compositions methods and systems.

The wording "antimicrobials" as used herein indicates a substance that kills or inhibits the growth of microorganisms such as bacteria, fungi, or protozoans.

The term "microorganism" is used herein interchangeably with the terms "cell," "microbial cells" and "microbes" and refers to an organism of microscopic or ultramicroscopic size such as a prokaryotic or a eukaryotic microbial species. The term "prokaryotic" refers to a microbial species that contains no nucleus or other organelles in the cell, which includes but is not limited to bacteria.

Certain antimicrobials can be in the form of drugs that either kill microbes (microbicidal) or prevent the growth of microbes (microbistatic). The wording "targeted antimicrobial" as used herein, indicates an antimicrobial that is capable of specifically killing or inhibiting growth of one or more microorganisms, and in particular of one or more bacteria. More particularly, a targeted antimicrobial is able to specifically kill or inhibit the growth of the one or more microorganisms, and in particular bacteria that express the antimicrobial or are related to the microorganism that express the antimicrobial.

The term "specific", as used herein with reference to the activity of a targeted antimicrobial, refers to the ability to kill or inhibit the growth of one or more specific microorganism with substantially less to no ability to kill or inhibit the growth of other microorganisms that may be present.

In an embodiment, targeted antimicrobials in the sense of the present disclosure can be identified among lytic enzymes expressed by the microorganism to be targeted.

In particular, a candidate targeted antimicrobial can be identified from the lytic enzymes expressed by the microorganism that are capable of targeting one or more moieties on the exterior surface of the microorganism, that provide the microorganism with structural support and/or protection.

Exemplary lytic enzymes in the sense of the present disclosures comprise muramidases, amidases, endopeptidases, L-alanyl-D-glutamate peptidases and other enzymes capable of target moieties presented on the exterior of a cell identifiable by a skilled person.

Exemplary one or more moieties targeted by the lytic enzymes comprise peptidoglycan, cellulose, hemicelluloses, glycoproteins, and in particular glycoprotein S-layers, pseudopeptidoglycan, polysaccharides, glucosamine polymers such as chitin, and portions thereof and additional moieties identifiable by a skilled person upon reading of the present disclosure.

Exemplary microorganisms comprise bacteria, algae, fungi and additional cells presenting moieties on the surface of the cells that are associated with structural support and/or protection of the cell.

In an embodiment, a candidate targeted antimicrobial can be identified by comparing sequences of the microorganism with sequences of a model lytic enzyme capable of targeting moieties presented on the surface of a microorganism and selecting sequences having an identity greater than about 40% or similarity greater than about 50% with the sequences of the entire model lytic enzyme or selected portions thereof, the selected portions associated with the lytic activity of the enzyme.

Exemplary model lytic enzymes comprise small phage-produced proteins responsible for lysis of an infected host cell, such as the ones described in documents identifiable by a skilled person including for example references (2, 4, 14, 15, and 16). In particular, in an embodiment, model lytic enzymes can be provided by one or more endolysins. An endolysin is a lytic enzyme or protein typically produced by a bacteriophage, that degrades the host cell wall, facilitating release of new bacteriophage from the infected bacterial cells at the end of the phage infection cycle (14, 15). Usually, fully functional endolysins accumulate in the host cytosol near the end of the phage infection cycle. Additional exemplary model lytic enzymes comprise previously identified lytic enzymes in another microorganism, possibly but not necessarily related to the microorganism of interest, such as muramidase, amidase, endopeptidase and L-alanyl-D-glutamate peptidase.

The comparing can be performed using various approaches identifiable by a skilled person including approaches that allow computationally identifying candidate antimicrobial herein described.

For example, in an embodiment, the comparing can be performed by in silico computer searches of the microorganism's genome using the sequences of the model lytic enzyme as a parameter. Known and publically available search tools include but are not limited to the Basic Local Alignment Search Tool (BLAST) from the National Institutes of Health (see the web page blast.ncbi.nlm.nih.gov/Blast.cgi at the time of filing of the present application) and additional tools identifiable by a skilled person. Several strategies can be employed for the computer searches, all identifiable by a skilled person. In an embodiment, the comparison by computer searches comprises performing an analysis of previous genome annotations directed to identify genes encoding lytic proteins. Annotation also often identifies genes that function in bacterial cell wall synthesis and processing and can include lytic enzymes.

Another in silico approach for comparing can be performed by directly comparing DNA sequences of previously identified lytic enzymes' genes or by directly comparing the predicted amino acid sequences of such proteins to predicted sequences in targeted genomes.

A further exemplary in silico approach for comparing can be performed by predicting the protein structure of known lytic proteins based on their predicted or determined amino acid sequences, and then searching available sequence databases (e.g. DNA databases) for sequences that encode proteins of similar predicted structure. Successfully targeted genes will encode antimicrobials that exhibit lytic activity against a targeted bacterial pathogen.

In an embodiment, the comparing can be performed by analysis based on local protein or DNA alignment studies that compare relatedness (identity and similarity) using a known sequence (e.g. model lytic protein and/or a portions thereof), or compilation of sequences (e.g. one or more model lytic protein and/or a portion thereof), used to search any available database (e.g. using BLAST) that contains genetic (DNA) or protein sequences or information to identify novel protein sequences.

The comparing according to any of the approaches mentioned herein is typically performed between nucleotidic or amino acidic sequences of the model lytic enzyme and microorganism genome. The comparing is typically performed considering sequences covering the entire model lytic enzyme, or the one or more portions of the model lytic enzymes associated with the lytic activity of the model lytic enzyme. Those portions can include not only the lytic domain of the model lytic enzyme but also additional domains responsible for stability, three-dimensional structure and any other features associated with an active protein. Those portions can vary from one model enzyme to another. A skilled person will be able to identify such portions based on the specific model enzyme used for identification. In an embodiment, the comparing can be performed using the entire sequence of the model lytic enzyme (see for example the comparison performed in Example 1). Sequences from the genome of the microorganism at issue that show at least about a 40% identity or about 50% similarity in outcome of at least will be selected. In some embodiments, sequences showing about 60% to 90% identity and/or similarity can be selected. In some embodiments, sequence having at least 90% identity or similarity and in particular about 95% or higher identity or similarity can be selected.

For example, in an embodiment, basic alignment and local basic alignments in programs such as Geneious 5.0.3 or ClustalW (see web page ebi.ac.uk/Tools/clustalw2/index.html at the time of filing of the present application) can be used to look for specific homologies. Using default settings, proteins with pairwise identity of 40% or higher can be typically selected.

For example, in embodiments wherein BLAST is used, proteins with a "Total Score" of about 100 or more and/or an E value of 0.001 or lower can be selected as candidate targeted antimicrobials.

In an embodiment, the identifying can be performed by performing a plurality of comparing using the same or different approaches. In some of those embodiments, performing a plurality of comparing using different approaches can be performed to account for the possibility that a little shared DNA sequence homology among genes encoding proteins with similar enzymatic activity can occur. In various occurrences, identifiable by a skilled person restricting one's search to direct DNA sequence comparisons can limit the number of genes encoding these lytic proteins.

In particular, in some embodiments, identifying candidate antimicrobials can be performed by performing a plurality of screen levels of the genome sequences of the microbe of interest. For example a first screening of the genome can involve analysis of published annotation studies that specifically identify such genes as muramidases or the other three categories of lytic proteins. The second screen is a BLAST search against known gene sequences encoding these lytic proteins in microbes that are closely related to the species of interest. The third screen involves a search for genes that have been implicated in cell wall biosynthesis or metabolism. These gene sequences are subjected to further scrutiny by comparing the amino acid sequences they encode to those of other known muramidases and other lytic proteins. The fourth screen involves BLAST searches based on the amino acid sequences of known muramidases and other lytic proteins. The fifth screen requires computational analysis of amino acid sequences of known muramidases and other lytic proteins to identify specific structural characteristics of this class of proteins followed by a computational search of genomes to identify genes encoding proteins that may have similar structure. For example small number of endolytic proteins have been structural characterized and the structure of portions of the proteins responsible for lytic activity are known. In this case, one can search for similar structures encoded in the genomes of pathogens of interest. One starts with the simplest steps outlined above and progresses to more complicated screen.

Exemplary procedures for identifying candidate antimicrobials are reported in Examples 1, 8 and 9 of the present application.

Once a candidate antimicrobial is identified, the candidate antimicrobial is then tested for antimicrobial activity on the same microorganism expressing the candidate antimicrobial or on a microorganism related to the microorganism expressing the candidate antimicrobial In an embodiment, the gene coding for the candidate antimicrobial can be amplified from the microorganism genome, cloned and expressed in an IVT system. Exemplary procedures are illustrated in the Example 2 of the present application. In another embodiment, the identified candidate antimicrobial can be acquired from other sources (e.g. if the enzyme is commercially available).

The candidate antimicrobial can then be subjected to one or more tests, where the candidate antimicrobial is contacted to the microorganism to determine an antimicrobial activity of the candidate antimicrobial on the microorganism. In an embodiment, a first screen can be provided by a spot test, e.g. with procedure exemplified in Example 3. Although this procedure can be performed with a purified protein, the procedure does not require purified protein. Additional procedure can be used to detect an antimicrobial activity that include lysis of the microorganism (see e.g. Example 4) or other relevant features to determine suitability for antimicrobial (including protein stability detectable with procedures such as the ones exemplified in Example 5) and specificity for the one or more microorganisms of interest (e.g. using the procedures such as the ones exemplified in Example 6).

In an embodiment, once one or more candidate genes are identified at each step, the genes can be all amplified from the microorganism genome of interest in a single set of experiments. In an exemplary approach, PCR primers suitable to amplify the genes of interest and facilitate their immediate cloning into a standard expression vector can be used to stream-line the process. Additionally, several gene products can be tested simultaneously (see Example 3 and 4 for an exemplary approach).

In embodiments, where the amplification is performed in a microorganism other than the original microorganism expressing the enzyme (typically E. Coli) another factor that that can be considered is codon preferences of the target microbe from which the gene is amplified relative to those where the amplification is performed. If codon preferences are significantly different between the original microorganism and the microbe from which the putative lytic protein gene is amplified, that gene may not be expressed to a desired level in the selected microorganism. In this situation, other approaches can be used in addition or in the alternative to an In Vitro Transcription (IVT) system including but not limited to re-synthesize the gene using chemical DNA synthesis to produce a gene that encodes the same protein amino acid sequence but that is optimized for expression in the WT system.

The candidate antimicrobials that have a detectable antimicrobial activity can be selected as targeted antimicrobial for the one or more microorganisms wherein the antimicrobial activity has been tested or can be predicted based on a genetic relationship.

The terms "detect" or "detection" as used herein with reference to an activity of a molecule indicates the determination of the existence, presence or fact of any indicator of the activity in a limited portion of space, including but not limited to a sample, a reaction mixture, a molecular complex and a substrate. The "detect" or "detection" as used herein can comprise determination of a chemical and/or biological indicator associated with the molecule's activity. Suitable indicators include but not limited to ability to interact, and in particular bind, other compounds, ability to activate another compound, production of one or more compounds or molecules associated with the activity and additional properties identifiable by a skilled person upon reading of the present disclosure. The detection can be quantitative or qualitative. A detection is "quantitative" when it refers, relates to, or involves the measurement of quantity or amount of the detected activity (also referred as quantitation), which includes but is not limited to any analysis designed to determine the amounts or proportions of one or more indicators of the activity. A detection is "qualitative" when it refers, relates to, or involves identification of a quality or kind of the activity in terms of relative abundance to another activity, which is not quantified.

An exemplary procedure, for identifying a targeted antimicrobial according to the present disclosure is reported in Example 7, of the present application.

Targeted antimicrobials obtainable by methods herein described comprise proteins that possess enzymatic and lytic activity that specifically damages cell walls thereby destroying the microorganism target. Typically targeted antimicrobials obtainable by methods herein described are structurally related to lysozyme (also known as muramidase) or other model lytic enzymes selected for the identification, and comprise a N-terminal portion of a protein responsible for lytic activity and a C-terminal portion responsible for target recognition and binding. In various embodiments, targeted antimicrobials differ from lysozyme (or other model lytic enzyme) because of their high specificity for a given microorganism (or group of microorganisms) that are targeted.

The term "lysozyme" as used herein indicates a broad-spectrum lytic enzyme that affects many species and comprise glycoside hydrolases, enzymes (EC 3.2.1.17) that damage bacterial cell walls by catalyzing hydrolysis of 1,4-beta-linkages between N-acetylmuramic acid and N-acetyl-D-glucosamine residues in a peptidoglycan and between N-acetyl-D-glucosamine residues in chitodextrins. Lysozyme is abundant in a number of secretions, such as tears, saliva, human milk, and mucus. It is also present in cytoplasmic granules of the polymorphonuclear neutrophils (PMN). Large amounts of lysozyme can be found in egg white. C-type lysozymes are closely related to alpha-lactalbumin in sequence and structure, making them part of the same family.

Targeted antimicrobials herein described differ from lysozyme and phage endolysins in that, under certain conditions, they are more active and more stable than the model lytic proteins and are encoded by genes from the target bacteria's own genome. Targeted antimicrobials herein described comprise lytic proteins, which target specific moieties of the microorganism's own cell wall and normally play a role in synthesizing and maintaining the peptidoglycan layer of a bacterial cell. In general targeted antimicrobials herein described are enzymes encoded by the target bacteria's own genes and have a function in cell wall biosynthesis and metabolism.

Applicants have unexpectedly found that under appropriate conditions wherein regulation of their expression and/or activity from the microorganism expressing them is not present, these proteins are able to affect destabilizing the peptidoglycan layer, which can result in preventing the host cell from maintaining osmotic equilibrium or in any case impact the viability of the cell.

Typical conditions where regulation of the expression and/or activity of the targeted antimicrobial is not present comprise concentrations higher than the concentration produced by the targeted microorganism and not confined to the locations within the cells where they are normally expressed, absence of inhibitors and other conditions identifiable by a skilled person. For example in embodiments where the microorganism is a spore-forming microorganism the conditions typically comprise any condition where the spore-forming microorganisms are in a vegetative state. In some embodiments suitable conditions comprise providing a concentration of antimicrobial herein described that is about 2:1 or greater than the concentration produced by the cell or by a related microorganism. In several embodiments, exposure of the cells to concentrations of a lytic protein suitable to be used as antimicrobial according to the present disclosure that are at least 2-3 orders of magnitude higher than the concentration normally produced by the cell (e.g. they are produced only in very minute amounts at very specific locations within the bacterial cells) or a cell that is genetically related, typically results in rapid bacterial cell lysis and death.

In particular, in an embodiment targeted antimicrobials herein described can kill or inhibit growth not only of the microorganism expressing the enzyme but also of genetically related microorganisms and, in particular, bacteria.

Genetically related microbes in the sense of the disclosure are those that have been identified by DNA-based methods (direct comparisons of genome sequences or indirect methods that given an indication of genome sequence and organization) as being very similar to a particular target species but, by other means (16S rDNA analysis, antigenic markers or other such methods) have been determined to not be the same species as the target. Genetically related organisms are those that, by analysis using different generally accepted phylogenetic methods [Amplified Fragment Length Polymorphism (AFLP), Single Nucleotide Polymorphism (SNP), Multi-locus Sequence Typing (MLST) and other methods] are deemed to be related when data sets are analyzed using Principle Component Analysis or similar peer-reviewed phylogenetic methods.

Typically, genetically related microorganisms in the sense of the present disclosure express at least one protein that with about a 40% or higher identity and/or about a 50% or higher similarity. Accordingly, for example a first microorganism expressing a first protein (e.g. identified as an antimicrobial by methods herein described), is related to a second microorganism expressing a second protein, if the second protein has about a 40% or higher identify or a 50% or higher similarity to the first protein. A closer genetic relationship can be evidenced in some embodiments, by sequences showing about 60% to 90% identity and/or similarity, sequences having at least 90% identity or similarity and in particular about 95% or higher identity or similarity between the microorganisms.

For example, members of the subgroup 1 Bacilli, which includes *B. anthracis* are all genetically related with a subset of these being extremely closely related to *B. anthracis*. *Yersinia pestis* is very closely related to *Yersinia pseudotuberculosis* but not as closely related to *Y. enterocolitica*. *Burkholderia mallei* and *B. pseudomallei* are very closely related while neither is as closely related to *B. thailandensis*. There are many examples of these relationships in the literature that are identifiable by a skilled person, such as for example the reference by Hoffmaster, et al. (9).

In several embodiments, effectiveness of a targeted antimicrobial herein described for a microorganism related to the microorganism expressing the antimicrobial is correlated to how closely related the microorganisms are. Accordingly, the higher the percentage identity/similarities between the at least one protein expressed by the microorganisms the higher is the expected effectiveness of the antimicrobial (see e.g. Example 6 of the present application).

In embodiments herein described, targeted antimicrobials are comprised of a specific class of proteins, encoded by bacterial genes and that includes muramidases, amidases, endopeptidases, L-alanyl-D-glutamate peptidases and other proteins that target specific components of the bacterial cell wall and are capable of exhibiting lytic activity, and in particular endolysin-like activity, when applied externally to targeted bacterial cells.

Endolysin-like activity indicates a form of hydrolytic activity that damages or destroys specific linkages between cell wall moieties resulting in degradation of the cell wall and resulting bacterial cell death that is typical of endolysin and identifiable by a skilled person. Endolysins are typically produced by a phage during the bacterial lytic infection cycle and serve to disrupt the bacterial cell wall to release progeny phage. Endolysin activity and bacterial enzyme-facilitated lytic activity are related in that they can modify, alter or damage bacterial cell walls. Muramidases and similar lytic proteins are derived from non-phage sources and are common to all bacteria. These proteins normally function, in vivo, to regulate cell wall synthesis and maintenance. "Endolysin-like activity" and "muramidase activity" are used to describe cell damage, usually resulting in inhibition of growth and also cell death that is caused by a targeted antimicrobial protein. Typically, muramidase activity is associated with a protein that is a member of one of four known classes of enzymes (muramidases, amidases, endopeptidases, L-alanyl-D-glutamate peptidases) and, possibly, some previously uncharacterized proteins.

In particular, in some embodiments lytic proteins identified as targeted antimicrobials with method herein described, comprise enzymes encoded in the host genome that have endolysin-like function, but with up to two orders of magnitude greater activity relative to a phage endolysin. Differences in activity between lytic enzymes can be measured using various technical approaches identifiable by a skilled person. For example difference in activity between a model lytic enzyme and a targeted antimicrobial, or between two targeted antimicrobials can be measured by applying the same concentration of protein (e.g. bacterial lytic protein or phage endolysin) to the same number of target bacterial cells in the same reaction volume and incubating under the optimal conditions for each enzyme for a specific period of time. The number of surviving cells is then measured by plating the treated cells on agar plates and counting the number of colonies that grow on the plates. If identical concentrations of the two proteins result in a difference in the number of surviving colonies one can determine the relative effectiveness of the enzymes. If, for example, treatment with the phage endolysin results in 100 colonies growing on the test plate and 0 colonies grow on the bacterial lytic protein plate, then the bacterial lytic protein is at least 100 times or two orders of magnitude (10×10) more effective that the phage endolysin infection cycle.

In an embodiment, the targeted antimicrobial obtained with methods herein described are recombinant proteins, which can be identical or modified with respect to the original enzyme (e.g. by adding structures such as a six histidine residue end tag to facilitate rapid purification of the protein). Other modifications are possible to improve (for example) solubility or other features of the targeted antimicrobial. For example, in some embodiments lytic proteins are not soluble at a desired concentration (typically at low concentrations such as nM or pM concentrations). Additional modifications of the protein (by making changes in the gene encoding the protein) or addition of other genetic sequences that facilitate protein solubility can be used to enhance the solubility properties of the lytic proteins, all identifiable by a skilled person upon reading of the present disclosure.

In embodiments, where a lytic protein (such as the one that destroys methecillin-resistant *S. aureus* (MRSA) cells) are reproduced in a non-native system (such as *E. Coli* in this case) further modification could be performed to adapt the sequence to the non-native system. For example, the DNA sequence of the gene that destroys methecillin-resistant *S. aureus* (MRSA) cells is not efficiently expressed in the *E. coli*-based IVT system because *E. coli* has preference for specific nucleotide triplets when producing proteins that are different from those preferred by *S. aureus*. By changing the DNA sequence for optimal expression in the *E. coli* IVT system, production of a lytic protein identical to that encoded by the *S. aureus* gene can be enhanced. It is also possible to alter the bacterial target by manipulating the DNA sequence of the portion of the gene that encodes the C-terminal end of the lytic protein because this part of the protein provides target specificity to the enzyme. In that way, production of a chimeric protein that will attack specific moities of a bacterial cell wall in a different targeted bacteria is expected.

Bacteria that can be targeted by the targeted antimicrobials herein described comprise several prokaryotic microbial species that include but are not limited to Gram-positive bacteria, Proteobacteria, Cyanobacteria, Spirochetes and related species, *Planctomyces, Bacteroides, Flavobacteria, Chlamydia*, green sulfur bacteria, green non-sulfur bacteria including anaerobic phototrophs, radio-resistant micrococci and related species, *Thermotoga* and *Thermosipho* thermophiles. More specifically, the wording "Gram positive bacteria" refers to cocci, non-sporulating rods and sporulating rods, such as, for example, *Actinomyces, Bacillus, Clostridium, Corynebacterium, Erysipelothrix, Lactobacillus, Listeria, Mycobacterium, Myxococcus, Nocardia, Staphylococcus, Streptococcus* and *Streptomyces*. The term "Proteobacteria" refers to purple photosynthetic and non-photosynthetic gram-negative bacteria, including cocci, non-enteric rods and enteric rods, such as, for example, *Neisseria, Spirillum, Pasteurella, Brucella, Yersinia, Francisella, Haemophilus, Bordetella, Escherichia, Salmonella, Shigella, Klebsiella, Proteus, Pseudomonas, Bacteroides, Acetobacter, Aerobacter, Agrobacterium, Azotobacter, Spirilla, Serratia, Vibrio, Rhizobium, Chlamydia, Rickettsia, Treponema* and *Fusobacterium*. Cyanobacteria, e.g., oxygenic phototrophs.

In an embodiment, targeted antimicrobials herein described can be used to target Gram positive bacteria, in particular Bacilli and more particularly, *Bacillus anthracis*, and certain, defined isolates of *Bacillus cereus* and *Bacillus thuringiensis* as exemplified in the Examples section (see reference 9, Example 1, branch F for phylogenetically related isolates that are impacted by BCZK2532).

In particular, experiments exemplified in the Examples section (see, in part, Example 2), indicate that the exogenous application of targeted antimicrobials can achieve in some embodiments, an antimicrobial response in *Bacillus anthracis* that is 1,000 to 10,000 times more effective than common antibiotics. Moreover, certain targeted antimicrobials herein described (e.g., encoded by the genome of *Bacillus cereus* E33L—the closest known relative of *B. anthracis*) have shown the ability to be more active and more specific against *B. anthracis* than several protein endolysins encoded by the genomes of bacteriophage that specifically infect and kill this pathogenic bacterium.

In an embodiment, a targeted antimicrobial herein described encoded by the genome of a pathogenic *Bacillus*, functions as an enzyme that specifically targets and destroys the cell walls of this pathogen and genetically related Bacilli when applied in nanomolar (nM) concentrations.

Figure 5:
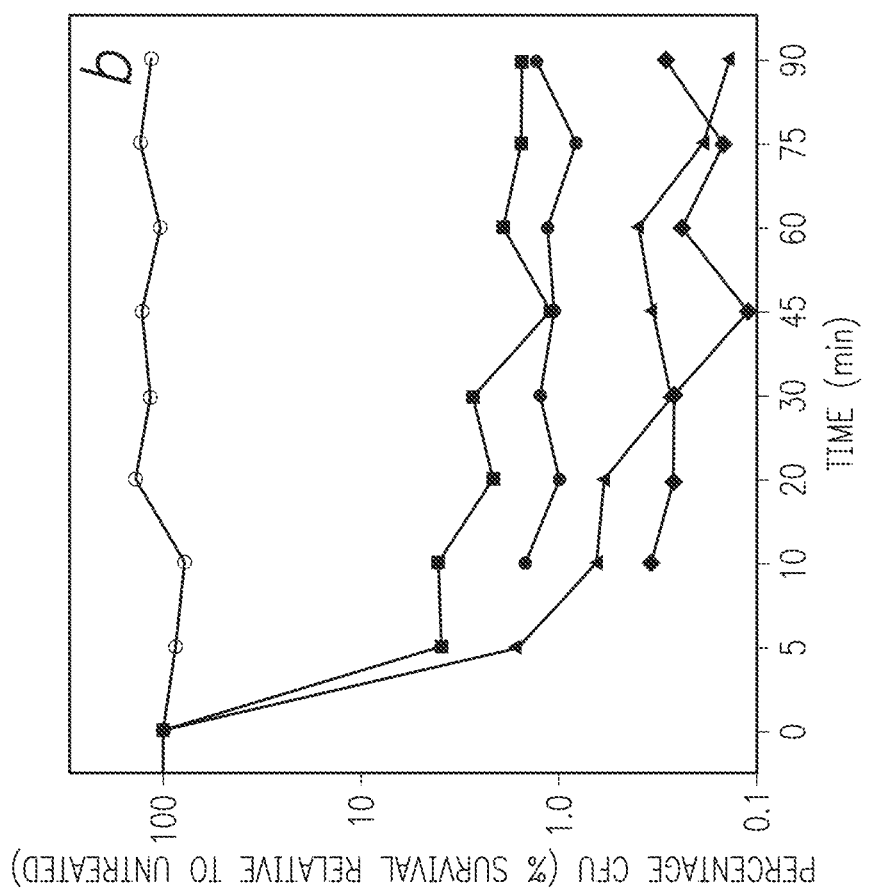
Figure 5:
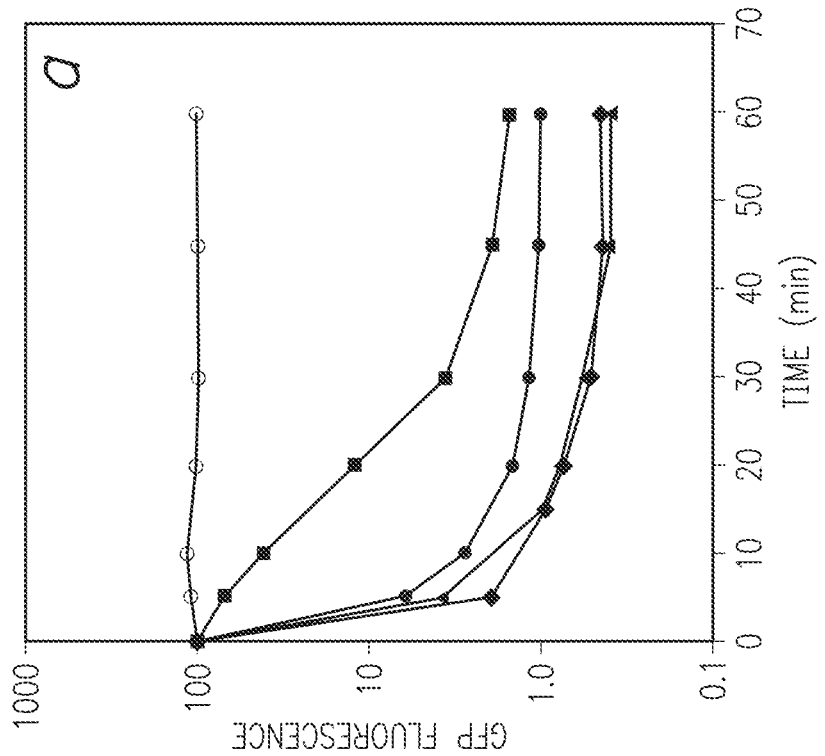

In an embodiment, the antimicrobial is BCZK2532 protein expressed by *B. cereus* and the targeted microorganisms comprise *B. cereus* and the related microorganisms *B. anthracis, B. thuringiensis* 97-27, *B. thuringiensis* HD1, *B. thuringiensis* HD560 and *B. thuringiensis* HD658. Very low concentrations of BCZK2532 protein are highly effective against the target microorganism. For example, exposure of *B. anthracis* cells to 33 ng/mL of this lytic protein for 5 minutes results in greater than 90% kill of the culture (see Example 4 and FIG. 5). Treatment with 1.65 to 3.3 µg/mL for 10 minutes results in lysis of more than 99% of the culture (FIG. 5b). Treatment of a culture containing approximately $5 \times 10^8$ cells/mL with 2.5 µg/mL BCZK2532 protein resulted in almost complete cell lysis in three minutes. In comparison, treatment or prevention of a *B. anthracis* infection with ciprofloxacin is usually performed by providing a desired serum concentration of 2.5 µg/mL.

Figure 7:
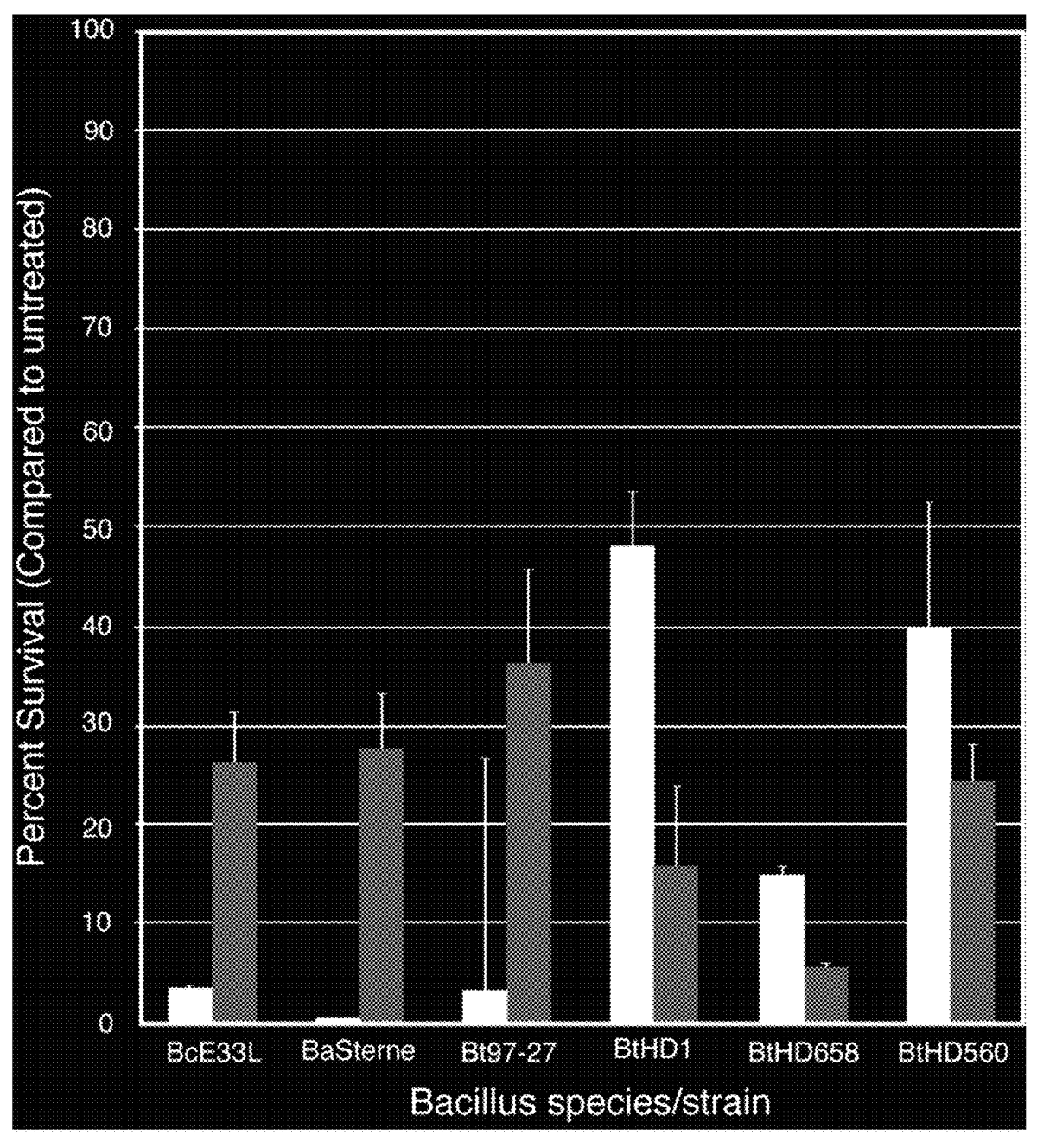

The BCZK2532 protein is encoded by the *B. cereus* E33L genome although the protein produced differs by only one conservative amino acid change from the same protein encoded by the *B. anthracis* genome. *B. cereus* E33L is the closest known relative of *B. anthracis*. FIG. 7 shows results of treatment of different *B. cereus* and *B. thuringiensis* strains with BCZK2532 lytic protein. The closest known relatives of *B. cereus* E33L are *B. anthracis* and *B. thuringiensis* 97-27 as defined by an abundance of phylogenetic and genome sequencing criteria. In contrast, *B. thuringiensis* HD1 and HD560 are only distantly related to *B. cereus* E33L while *B. thuringiensis* HD658 is more closely related by not as close as the other two related isolates. Experiments exemplified in Example 6 of the present application (percent survival as a function of relatedness) indicate that the more closely related an isolate is to the isolate from which the lytic protein gene was derived, the more effective the lytic protein is in lysing cells of that isolate.

In an embodiment, targeted antimicrobials herein described can be used to target Gram-negative bacteria such as *Yersinia pestis, Franciscella tularensis, Burkholderia* pseudomallei and other Gram-negative bacilli and cocci. Some of these microorganisms include: *Hemophilus influenzae, Klebsiella pneumoniae, Legionella pneumophila, Pseudomonas aeruginosa, Escherichia coli, Proteus mirabilis, Enterobacter cloacae, Serratia marcescens, Helicobacter pylori, Salmonella enteritidis,* and *Salmonella typhi.* Polymyxins, antibiotics that disrupt the structure of Gram-negative outer membranes can be used, in themselves, as antibiotics and there is renewed interest in their use due to increased antibiotic resistance in Gram-negative bacterial pathogens. However, these antibiotics are relatively neurotoxic and nephrotoxic, so high concentrations can be contraindicated in some circumstances. However, very low concentrations of these antibiotics in combination with lytic proteins encoded by a Gram-negative pathogen's own genes are expected to result in rapid destruction of the Gram-negative pathogen. Low concentrations of polymyxins will increase the permeability of the Gram-negative outer membrane, facilitating exposure of the inner cell wall to the lytic proteins (muramidases and other classes) resulting in rapid cell lysis. Combinations of lytic proteins and polyamines can be used to disinfect wounds and surfaces in a clinical or environmental setting when systemic treatment is not required. A skilled person will be able to identify the specific concentrations of antibiotic and antimicrobial upon reading the present disclosure.

Additional exemplary embodiments of bacteria that can be targeted with an antimicrobial herein described comprise, any bacterial species that contains genes encoding this class of lytic proteins can be effectively targeted using this approach. A review of some pathogenic bacteria genome sequences reveals that a significant number contains at least six to eight genes encoding this class of proteins. Not all lytic proteins are expected to have the same effectiveness (for example BCZK2532), so testing of the qualitative and quantitative antimicrobial activity of a lytic enzyme identified as a candidate antimicrobial is required to determine relative activity, enzyme stability and other properties and is necessary to identify the specific lytic enzyme that is the best choice for a particular use.

In an embodiment, methods herein described can be performed to culture an unknown new pathogen, extract DNA from the new pathogen and subject the DNA to deep sequencing to provide an unfinished genome sequence using available DNA sequencing, sequence assembly and annotation technology. In the embodiments, methods herein described are expected to allow, at least in some embodiments, identification of genes encoding these enzymes, cloning, expression and purification of the lytic proteins and production of this material within a short period of time, (e.g. a week) without need of identifying the pathogen.

Targeted antimicrobials herein described can be used in connection with various applications wherein an antimicrobial activity is desired.

In particular, targeted antimicrobials herein described can be used in an antimicrobial method that is specific for a microorganism and/or microorganisms genetically related thereto. The method comprises contacting the microorganism with a targeted antimicrobial herein described that is specific for the microorganism, the contacting performed in vitro or in vivo for a time and under condition to specifically kill or inhibit the growth of the microorganism.

In some embodiments, wherein the contacting is performed in vivo, the contacting can be performed by administering the targeted antimicrobial to an individual in a therapeutically effective amount to treat or prevent a condition associated with the microorganism in the individual.

For example in various embodiments, targeted antimicrobials herein described are expected to be suitable in medications that include topical remedies as well as therapies for individuals.

In particular, targeted antimicrobials herein described can be used in a method to treat a condition associated with the presence of a microorganism in an individual that comprises administering to the individual a therapeutically effective amount of targeted antimicrobial. The term "individual" as used herein includes a single biological organism wherein inflammation can occur including but not limited to animals and in particular higher animals and in particular vertebrates such as mammals and in particular human beings.

The term "condition" as used herein indicates the physical status of the body of an individual, as a whole or of one or more of its parts, that does not conform to the normal, healthy physical status of the individual, as a whole or of one or more of its parts, that is associated with a state of complete physical, mental and possibly social well-being. Conditions herein described include but are not limited to disorders and diseases wherein the term "disorder" indicates a condition of the living individual that is associated to a functional abnormality of the body or of any of its parts, and the term "disease" indicates a condition of the living individual that impairs normal functioning of the body or of any of its parts and is typically manifested by distinguishing signs and symptoms. Exemplary conditions include but are not limited to injuries, disabilities, disorders (including mental and physical disorders), syndromes, infections, deviant behaviors of the individual and atypical variations of structure and functions of the body of an individual or parts thereof.

The wording "associated to" as used herein with reference to two items indicates a relation between the two items such that the occurrence of a first item is accompanied by the occurrence of the second item, which includes but is not limited to a cause-effect relation and sign/symptoms-disease relation.

Conditions associated with an inflammation include but are not limited to: blood sepsis (toxic shock), MRSA infections, MDR infections, XDR infections, probiotic restoration of gut bacteria (natural flora), community acquired infections, difficult to treat infections such as biofilms in auditory canals, non-vascular joint infections, ocular infection and oral infections. First applications are not expected to involve systemic treatment and are expected to focus on organs and tissues that can be directly accessible to treatment (e.g. skin, sinus, ear and eye infections, and/or surgical wounds).

The term "treatment" as used herein indicates any activity that is part of a medical care for or that deals with a condition medically or surgically.

The term "prevention" as used herein indicates any activity, which reduces the burden of mortality or morbidity from a condition in an individual. This takes place at primary, secondary and tertiary prevention levels, wherein: a) primary prevention avoids the development of a disease; b) secondary prevention activities are aimed at early disease treatment, thereby increasing opportunities for interventions to prevent progression of the disease and emergence of symptoms; and c) tertiary prevention reduces the negative impact of an already established disease by restoring function and reducing disease-related complications.

An effective amount and in particular a therapeutically effective amount of targeted antimicrobial comprises concentrations of the lytic protein comparable to clinically relevant concentrations of specific antibiotics. For example, a clinically relevant ciprofloxacin concentration is 2.5 µg/mL. Results obtained by Applicants show rapid, effective cell lysis at concentrations of 1.65 µg/mL.

In an embodiment, the targeted antimicrobial herein described can be administered in combination with additional reagents that are suitable to enhance or support the activity of the targeted antimicrobials herein described. For example, in an embodiment, polyamines (e.g., protamine, polyethylenimine, and polymyxin B nonapeptide) can be provided in connection with treatment of infections to increase the permeability of the outer membrane of Gram-negative bacteria. Adding such compounds to endolytic protein preparations is expected to significantly increase sensitivity of Gram-negative bacteria to these lytic proteins (13) facilitating their use as antimicrobial agents against these pathogens. The use of such a combination is also expected to significantly reduce the concentration of polyamines required, significantly reducing the toxic effects such compounds have on the treated individual and on the concentration that can be considered therapeutically effective.

Additional exemplary applications where targeted antimicrobials herein described can be used comprise treating food stocks to eliminate food-borne pathogens in a manner similar to that described in (5, 19). Also an application in disinfection of equipments or environments (e.g. medical or surgical equipment, medical surfaces or operating rooms), especially in environments (e.g. military field clinics and hospitals) where nosocomial infections are particularly problematic, is also expected.

In particular, in an embodiment, one or more targeted antimicrobials can be contacted with a medium suitable to host the one or more related microorganisms that are targeted by the targeted antimicrobials. In the method the one or more related microorganisms might or might not be present in the medium. In method the contacting can be performed for a time and under conditions to specifically kill or inhibit the growth of the one or more related microorganisms if present in the medium.

Exemplary media comprise solid or fluidic media, such as surface s (e.g. externally accessible surface), other solid media, air, water or other fluidic medium, soil and additional media identifiable by a skilled person. The antimicrobial method can be used to prevent and/or eradicate contamination.

Topical disinfection of externally accessible surfaces and in particular of surfaces of hospital, clinical and environmental surfaces is expected to not be unlike experiments already conducted on bacterial cultures and that are the basis for identification of therapeutically effective amount. However, the presence of proteases and other adverse environmental aspects can decrease the effectiveness of the proteins depending on the environment they are deployed and a higher concentration can be required to obtain the same lytic results. A skilled person will be able to understand how to modulate the concentration in view of the parameters.

Further uses comprise also uses to specifically lyse target bacteria, including lysis of resistant Bacilli, during DNA isolation and protein isolation methods.

In particular, in an embodiment, targeted antimicrobials here described can be used in a method for in vitro molecule production. The method comprises contacting the microorganism containing a molecule of interest with a targeted antimicrobial herein described for the microorganism for a time and under conditions to provide a lysed microorganism and extracting the molecule of interest from the lysed microorganism.

In additional embodiments, targeted antimicrobials can be used in connection with automated DNA-based assays and other process wherein lysis of the cell population without mechanical disruption, (e.g. to make subsequent DNA purification significantly less challenging) is desired.

In other embodiments, targeted antimicrobials can be applied to a complex environmental sample, to lyse only those cells susceptible to the endolysin, thus enriching DNA from targeted organisms. These lytic proteins may also have utility in the decontamination of materials accidentally or intentionally contaminated with bacterial pathogens, especially when harsh disinfectants cannot be applied. Accordingly, in certain embodiments targeted antimicrobials can have important applications for environmental remediation and bioenergy production.

In some embodiments, one or more targeted antimicrobials herein described can be comprised in a composition together with a suitable vehicle. The term "vehicle" as used herein indicates any of various media acting usually as solvents, carriers, binders or diluents for the targeted antimicrobials comprised in the composition as an active ingredient.

In some embodiments, where the composition is to be administered to an individual the composition can be a pharmaceutical composition, and comprises the targeted antimicrobials herein described and a pharmaceutically acceptable vehicle.

In some embodiments, the targeted antimicrobials herein described can be included in pharmaceutical compositions together with an excipient or diluent. In particular, in some embodiments, pharmaceutical compositions are disclosed which contain the targeted antimicrobials herein described, in combination with one or more compatible and pharmaceutically acceptable vehicle, and in particular with pharmaceutically acceptable diluents or excipients.

The term "excipient" as used herein indicates an inactive substance used as a carrier for the active ingredients of a medication. Suitable excipients for the pharmaceutical compositions herein disclosed include any substance that enhances the ability of the body of an individual to absorb the targeted antimicrobials herein described. Suitable excipients also include any substance that can be used to bulk up formulations with the targeted antimicrobials to allow for convenient and accurate dosage. In addition to their use in the single-dosage quantity, excipients can be used in the manufacturing process to aid in the handling of the targeted antimicrobials. Depending on the route of administration, and form of medication, different excipients may be used. Exemplary excipients include but are not limited to antiadherents, binders, coatings disintegrants, fillers, flavors (such as sweeteners) and colors, glidants, lubricants, preservatives, sorbents.

The term "diluent" as used herein indicates a diluting agent which is issued to dilute or carry an active ingredient of a composition. Suitable diluent include any substance that can decrease the viscosity of a medicinal preparation.

In certain embodiments, compositions and, in particular, pharmaceutical compositions can be formulated for systemic administration, which includes enteral and parenteral administration.

Exemplary compositions for parenteral administration include but are not limited to sterile aqueous solutions, injectable solutions or suspensions including the targeted antimicrobials herein described. In some embodiments, a composition for parenteral administration can be prepared at the time of use by dissolving a powdered composition, previously prepared in lyophilized form, in a biologically compatible aqueous liquid (distilled water, physiological solution or other aqueous solution).

Exemplary compositions for enteral administration include but are not limited to a tablet, a capsule, drops, and suppositories.

In some embodiments, targeted antimicrobial, model lytic proteins can be used singly or in combinations with other targeted antimicrobial lytic proteins in an antimicrobial system, and/or in a system for in vitro molecule production. In some embodiments, the targeted antimicrobial can be comprised in composition with suitable vehicle, carrier and/or auxiliary agents. In some embodiments, the system can be in kit form.

Kits will include one or more lytic proteins in liquid or lyophilized form along with appropriate buffers for use of the proteins and directions for their use. Uses include disinfection of contaminated surfaces (hospital, clinical, building or environmental decontamination), treatment of selected bacterial infections as a topical gel or salve, mouth rinse, eye or nasal rinse or spray to prevent or treat infections and as chemotherapy for blood sepsis. Uses also include single lytic proteins or cocktails of these in reagents that provide rapid, high efficiency lysis for automated extraction of DNA from complex samples without the need for physical disruption methods.

Additional components can include suitable reagents for detecting antimicrobial activities, reference standards, and additional components identifiable by a skilled person upon reading of the present disclosure. In particular, the components of the kit can be provided, with suitable instructions and other necessary reagents, in order to perform the methods here disclosed. The kit will normally contain the compositions in separate containers. Instructions, for example written or audio instructions, on paper or electronic support such as tapes or CD-ROMs, for carrying out the assay, will usually be included in the kit. The kit can also contain, depending on the particular method used, other packaged reagents and materials (i.e. wash buffers and the like).

Further details concerning the identification of the suitable vehicle, carrier or auxiliary agent of the compositions of the kit, and generally manufacturing and packaging of the kit, can be identified by the person skilled in the art upon reading of the present disclosure.

An antimicrobial system typically comprises at least two of one or more targeted antimicrobial for a microorganism; suitable reagents and an additional antimicrobial, for simultaneous combined or sequential use in an antimicrobial method targeting the microorganism An in vitro molecule production system typically comprises at least two of one or more targeted antimicrobial for a microorganism; suitable reagents and an additional antimicrobial, for simultaneous combined or sequential use in an in vitro molecule production method targeting the microorganism.

The above applications can be particularly used in newly identified microbes and in particularly a new pathogen in particular but not necessarily if a source of therapeutically useful endolysins is not known.

EXAMPLES

The targeted antimicrobials and related compositions, methods and systems herein disclosed are further illustrated in the following examples, which are provided by way of illustration and are not intended to be limiting In particular, the following examples illustrate exemplary targeted antimicrobial BCZK2532 and methods for identifying and providing BCZK2532 and additional targeted antimicrobials. A person skilled in the art will appreciate the applicability of the features described in detail for BCZK2532, *Bacillus anthracis*, *Bacillus cereus* and *Bacillus thuringiensis* and related cells/cultures systems suitable for identifying, and producing BCZK2532 for additional targeted antimicrobials according to the present disclosure directed to bacteria or other microorganisms. In particular, it is expected that microorganisms other than bacteria that share similar target moieties on the exterior portion of the cell (e.g. wall structure) provide target substrates for targeted antimicrobials specific to those moieties according to the present disclosure.

The following material and methods were used for all the methods and systems for detection of immunomodulatory substances exemplified herein.

Growth of Bacterial Cultures.

Cultures of the different *Bacillus* isolates were started from single colonies and grown at 30° C. or 35° C. overnight in Nutrient Broth (EMD Chemicals, Gibbstown, N.J.). The following day a small aliquot of the overnight culture was added to fresh media. The suspension was incubated at 30° C. or 35° C. with shaking at 150 rpm to an $OD_{600}$ of 0.45 to 0.5 in Nutrient Broth. Prior to treatment with endolysins, cells were collected by centrifugation at 3,200 g for 10 min. The supernatant was decanted and the bacterial pellet was suspended in the same volume of ambient temperature phosphate buffered saline solution, pH 7.4 (1.06 mM $KH_2PO_4$, 155 mM NaCl, 2.97 mM $Na_2HPO_4.7H_2O$), (Invitrogen, Inc., Carlsbad, Calif.) prior to endolysin treatment. The different bacterial species and strains used in this study are listed in Table 1.

TABLE 1

Bacillus species and strains used in this study

| Species | Strain | GFP Fluorescence | Source |
|---|---|---|---|
| Bacillus anthracis | Sterne | Negative | Dugway Proving Grounds, Utah |
| Bacillus anthracis | Sterne UT238* | Positive | Theresa Koehler, UT, Houston Medical Center, TX |
| Bacillus anthracis | Sterne 7702/pUTE610** | Positive | Theresa Koehler, UT, Houston Medical Center, TX |
| Bacillus cereus | E33L | Negative | Tetracore, Inc., Rockville, MD |
| Bacillus thuringiensis | serovar konkukian 97-27 | Negative | Laboratoire de Biologie, Hopital des Armees Begin, Paris, France |
| Bacillus thuringiensis | serovar kurstaki HD1 | Negative | ARS Culture Collection (NRRL), Peoria, IL |
| Bacillus thuringiensis | serovar israelensis HD658 | Negative | ARS Culture Collection (NRRL), Peoria, IL |
| Bacillus thuringiensis | serovar kenyae HD560 | Negative | ARS Culture Collection (NRRL), Peoria, IL |

*This isolate contains a single copy of the gene for green fluorescent protein (GFP) gfpmut3a fused to a 645-bp PCR product containing the constitutively active promoter of the *B. anthracis* metalloprotease gene, inhA (BA1295) (22).
**Plasmid pUTE610 carries the gene for green fluorescent protein (GFP) gfpmut3a fused to a 645-bp PCR product containing the constitutively active promoter of the *B. anthracis* metalloprotease gene, inhA (BA1295) (22).

DNA Isolation and Purification.

Five milliliters of nutrient broth was inoculated with bacteria from a single colony and cultures were incubated overnight at 30 or 35° C. with shaking at 150 rpm. Bacterial cells were collected by centrifugation at 1,000×g for 15 min.

DNA was extracted from the pelleted bacteria using a MasterPure™ Gram Positive DNA Purification Kit from Epicentre Biotechnologies (Madison, Wis.) following the protocol provided by the manufacturer. If only small amounts of DNA was needed, a single bacterial colony was lifted from an agar plate using a sterile toothpick and suspended in 50 µl of a buffer containing 1% (v/v) Triton X-100, 20 mM Tris-HCl, pH 8.5 and 2 mM EDTA. Bacterial cells were released into this solution by briefly vortexing the sample. The tube containing the suspension was capped and incubated at 95° C. for 10 minutes. Cells and debris were removed by centrifugation at 12,000×g for 5 minutes and the supernatant was collected and used as a source of DNA. Five µl of DNA prepared in this manner was ample for PCR amplification of any target.

Identification of Genes Encoding Bacterial Endolytic Proteins.

There is insufficient nucleotide sequence homology among endolysin genes from different bacteria and bacteriophage to allow identification of the majority of these genes by direct comparison of nucleotide sequences. The bacteriophage TP21-T (Ply21) endolysin amino acid sequence was therefore used as a query sequence to identify related bacterial genome- and prophage-encoded proteins within published pathogenic bacterial pathogen genome sequences. A direct comparison of endolysin gene sequences from specific bacterial genomes was completed to demonstrate similarities and differences among these genes in closely related bacterial species. Bacterial genomes were screened with an emphasis on *B. anthracis* genome sequences and genome sequences from several *Bacillus* isolates that have previously been demonstrated to be very closely related to this pathogen (6, 9). BLASTP software provided by the National Center for Biotechnology Information (NCBI, see www website ncbi.nlm.nih.gov) was used to query available protein sequence databases. BLASTN software from the same source was used to query available DNA sequence databases.

Cloning a putative endolytic protein gene. A putative endolytic protein gene, BCZK2532, was identified in the chromosome of *B. anthracis* E33L (Accession no. NC006274) (6). PCR primers suitable to amplify this gene sequence from total genomic DNA and containing NcoI-NdeI restriction endonuclease recognition sequences at the 5' end and SmaI-BamHI restriction endonuclease recognition sites at the 3' end were designed. Inclusion of these restriction sites allowed direct ligation of the amplified fragment containing the endolysin gene into the pIVEX2.4d in vitro translation (IVT) expression vector (Roche Applied Science, Indianapolis, Ind.). The forward (5'-GGC-CATGGGGCATATGGGTTATATTGTAGATATTTCG-3' (SEQ ID NO:6)) and reverse (5'-CCCCCGGGATCCTT-TAACTTCATACCACCAAC-3' (SEQ ID NO:7)) were purchased from Operon Biotechnologies, Inc. (Huntsville, Ala.). The AmpD BCZK2532 gene was amplified from *B. cereus* E33L DNA in a reaction containing 10 mM Tris-HCl (pH 8.3), 50 mM KCl, 1.5 mM MgCl2, 0.001% (wt/vol) gelatin, 0.2 mM of each dNTP, 20 pmol of each primer, 2.5 U of Platinum Taq High Fidelity Polymerase (Invitrogen, Inc., Carlsbad, Calif.) and 20 ng template DNA. Template DNA was initially denatured by heating at 94° C. for 2 min. This was followed by 30 cycles of denaturation at 94° C. for 30 seconds, annealing at 50° C. for 30 seconds, and primer extension at 68° C. for 2 minutes. Incubation at 68° C. for 8 min followed to complete extension. PCR amplification was conducted in an Applied Biosystems GeneAmp™ PCR System 9700 (Applied Biosystems, Inc., Foster City, Calif.). The resulting amplicons were directly ligated into plasmid pCR2.1/TOPO and transformed into competent *E. coli* DH5α™-T1® cells using the TOPO TA Cloning® kit (Invitrogen, Inc.). Following verification of the cloned sequence by Sanger sequencing on an ABI Prism® 3100 Genetic Analyzer (Applied Biosystems, Foster City, Calif.), the sequence-verified gene was sub-cloned into the pIVEX2.4d plasmid (Invitrogen, Inc.), adding a sequence encoding a 6 X histidine tag to the DNA sequence encoding the N-terminus of the protein. The pIVEX2.4d/BCZK2532 plasmid was transformed into competent *E. coli* DH5α™-T1® cells. Cells containing this construct were identified and cultures were grown as a source of plasmid for subsequent IVT reactions.

Protein Expression and Purification.

Two μg of purified pIVEX2.4d/BCZK2532 plasmid DNA was used to drive in vitro synthesis of endolytic enzyme using an RTS 500 ProteoMaster *E. coli* HY Kit (Roche Applied Science) (1). Reactions were incubated at 30° C. for 18 hours with shaking (900 rpm). Newly synthesized histidine-tagged endolytic protein was purified from cell lysate under native conditions as follows. Ni-NTA Superflow resin (0.5 mL) (Qiagen, Inc, Valencia, Calif.) was equilibrated with Native Lysis Buffer (50 mM $NaH_2PO_4$, 300 mM NaCl, pH 8.0). The IVT lysate containing amplified BCZK2532 endolytic protein was mixed and incubated with the Ni-NTA Superflow resin for 2 hours at 4° C. The resin containing the bound BCZK2532 protein was then washed twice with 10 mL Native Lysis Buffer and four times with 10 mL Native Wash Buffer (50 mM $NaH_2PO_4$, 300 mM NaCl, 10 mM imidazole, pH 8.0). The His-tagged BCZK2532 protein was eluted from the column with 2 mL Native Elution buffer (50 mM $NaH_2PO_4$, 300 mM NaCl, 400 mM imidazole, pH 8.0), collected in 0.5 mL fractions. One to ten μl of each fraction was combined with an equal volume of LDS loading buffer (Invitrogen, Inc.) and heated for 10 min at 70° C. Proteins were electrophoretically separated by SDS-PAGE and stained with Coomassie Brilliant Blue. Purified proteins were transferred to 1× protein storage buffer (50 mM sodium phosphate buffer, pH 8.0, 200 mM NaCl, 5% (v/v) glycerol, and 1 mM dithiothreitol) by dialysis using 6,000-8,000 molecular weight cut off dialysis tubes (EMD Chemicals). All buffers contained Complete, EDTA-free Protease Inhibitor cocktail (Roche Applied Science).

Protein Characterization.

IVT-expressed BCZK2532 protein, purified or as part of a total IVT *E. coli* lysate was initially assayed for lytic activity in the following manner. *B. anthracis* strain Sterne was grown to an $OD_{600}$ of 0.45, collected by centrifugation at 3200×g for 10 minutes and the bacterial pellet was suspended in one-fourth the original volume of fresh nutrient broth. One hundred microliters of this cell suspension was added to 3 mL warm (47° C.) nutrient broth top agar (nutrient broth containing 0.75% w/v Difco agar) and immediately poured onto a nutrient broth agar plate at room temperature. The top agar was allowed to solidify for 5 minutes. Ten microliters of either the IVT *E. coli* lysate containing the BCZK2532 protein, purified BCZK2532 protein or some other endolysin was spotted onto the top agar. An IVT lysate expressing green fluorescent protein (GFP) or purified GFP from an IVT lysate generated as a control IVT reaction and purified using the same resins and buffers used to purify the lytic proteins, was used as a negative control. Nisaplin (Danisco, Inc, New Century, Kans.), a natural bacteriocin produced by fermentation of *Lactococcus lactis* that rapidly lyses bacteria, was used as a positive control. Plates were incubated overnight at 35° C. and scored based the presence or absence of a bacterial lawn where the different products were placed on the plate. A lack of growth at the application site indicated lysis of the bacterial cells.

Flow Cytometry.

Flow cytometry was performed using a Becton-Dickenson FACSan flow cytometer. GFP fluorescence was recorded in the FL-1 channel. Flow data was analyzed using Cell-Quest software (Becton-Dickenson, Franklin Lakes, N.J.). A *B. anthracis* Sterne 7702 containing a plasmid (pUTE610) encoding expression of GFP (22) was kindly provided by Dr. Theresa Koehler. A single colony of this isolate was inoculated into 5 mL nutrient broth containing 5 µg/mL erythromycin (EMD Chemicals) and grown with shaking (150 rpm) at 30° C. overnight. The following day, the overnight culture was used to start a new culture and the new culture was grown in nutrient broth containing erythromycin at 30° C. with shaking to an $OD_{600}$ of 0.45-0.5. Cells were collected by centrifugation as described above, washed by suspension of the cell pellet in 1×PBS, pH 7.4, centrifuged as before then suspended again in the original culture volume of 1×PBS, pH 7.4. Cells were divided into ten aliquots for the lysis experiments. Zero, 0.5, 1, 5, 10, or 50 nM BZCK2532 protein were added to the different cell aliquots. Cell suspensions containing the different amounts of this lytic protein were incubated at 30° C. and cell lysis and viability were monitored by flow cytometry and by plating portions of each aliquot on nutrient agar plates, then incubating the plates overnight at 30° C. to determine the number of surviving cells as measured by changes in the CFU of each suspension. The total number of fluorescent events in 10 seconds was counted for each flow cytometry data point.

Flow cytometry data were used to determine the enzyme kinetic properties of BCZK2532. The geometric mean of triplicate GFP-fluorescent events was divided by the pre-treated geometric mean of the GFP-fluorescent events for each sample so that the percentage GFP fluorescence of each untreated sample equaled 100% and the treated samples had values between 0 and 100%. The $K_m$ and $V_{max}$ were determined by plotting the inverse of the slope at 5 minutes vs. the percentage of GFP fluorescence remaining for the different BCZK2532 endolytic protein concentrations. The dissociation constant, $k_{-1}$. Was determined using the decay equation % $GFP_t = fmax(e^{-k_{-1}t})$ and fit by ByeGraph v.1.5 (Yasuyuki Hirai, see web site members2.jcom.home.ne.jp/yasu.hirai/). Specific activity was calculated as the change in percentage of GFP in the FL-1 flow channel per mg protein per minute.

Measuring Lytic Activity on Other *Bacillus* Isolates.

The impact of exposing different *Bacillus* species to BCZK2532 endolytic protein was determined by growing different *B. anthracis, B. cereus* and *B. thuringiensis* isolates to an $OD_{600}$ of 0.45 to 0.5 in nutrient broth at 35° C. or 30° C., collecting and washing the cells as described previously for the *B. anthracis* Sterne culture, the suspending the pellet in 1×PBS. Cell suspensions (2.5 mL) were treated with 100 nM BCZK2532 or Ply21 or incubated without enzyme for 1 hour at 35° C. Cells were then diluted and different dilutions were plated on nutrient agar plates. Plates were incubated overnight at 30° C. or 35° C., depending on the *Bacillus* isolate, to determine the number of cells surviving the treatment.

Example 1: Identification of Candidate Antimicrobial from the *B. cereus* E33L Genome The amino acid sequence encoded by the Ply21 gene from the *B. anthracis* bacteriophage TP-21-T (21) was used to identify genes with similar sequence in the *B. anthracis* and *B. cereus* genomes. In particular, genes identified in the *B. anthracis* Ames ancestor (Accession no. NC007530) and *B. cereus* E33L (Accession no. NC006274) were chosen for further evaluation. The search was performed in the NCBI database.

Global sequence alignments identified multiple putative glycosyl hydrolases (endolysins) in *B. anthracis* and its close relative, *B. cereus* E33L (6). The results of an exemplary alignment are illustrated in FIG. 1, wherein homologous residues among the different genes of the bacteria are identified, and the lack of sequence homology between the bacteriophage endolysin and the different bacterial lytic proteins noted by a comparison of successive amino acids in groups found in the bacterial proteins but absent in the bacteriophage endolysin protein amino acid sequence.

In particular, Applicants considered the 10 open reading frames upstream and downstream of the putative endolysin. If the lytic model is a prophage endolysin, it is expected to have neighboring holin genes, and other genes found in bacteriophage genomes.

Three homologous pairs were identified; BKCK2532 and BA2805; BCZK2195 and BA2446; and BA4073 and Ply21. BCZK2195 and BCZK2532, from the *B. cereus* E33L genome, encode bacterial endolytic proteins. BA2446, with close nucleotide sequence homology to BCZK2195; and BA2805, with close homology to BCZK2532 are both encoded by the *B. anthracis* chromosome.

In contrast, BA4073, with sequence homology to the bacteriophage TP-21-L Ply21 gene, appears to be associated with a prophage sequence within the *B. anthracis* genome and probably is a phage-encoded endolysin. BA4073 was previously reported as PlyL (18).

The BLAST score for the above selection and the corresponding homology are indicated in Table 2 below.

TABLE 2

| Approach | Protein | Score | Identity |
|---|---|---|---|
| Using *Bacillus* phage 0305phi8-36. (TP21-T found this phage first) | BCZK2532 | 185 bits | 45% |
| | BA2805 | 185 bits | 45% |
| Using TP21-T: | BA4073 | 259 bits | 63% |

In the attempt to limit the number of proteins used to analyze and rationalize the experiments typically (but not necessarily) one or two proteins that have a high bit score, (e.g. in the 500 bits and up) are selected. Then several more genes in the mid-range, (e.g. 200-500) are selected, followed by additional genes in the low range, (e.g., 100-200). According to this approach selection of enzymes having a broad range of activity is expected. The specific score and corresponding homology that is used as a threshold and the number of screen levels depend on the experimental approach and are identifiable by a skilled person. The principle is that a more comprehensive approach minimizes the chances that a really good protein, with respect to it lytic activity could be not selected.

BA2446 was reported by Rollins, et al. (20) to have *B. anthracis*-specific lytic activity although the enzyme was tested only against *B. anthracis*, one *B. cereus* isolate, one *B. subtilis* isolate and a single *E. coli* strain and the concentrations of purified protein needed to generate lysis were significantly higher than those reported here. Six genes were chosen for further study. BA2446, BA2805 and BA4073, encoding putative endolysin genes were chosen from *B. anthracis*. BCZK2195 and BCZK2532, encoding very similar proteins, were chosen from the *B. cereus* E33L genome, and BALH_3313, encoding an endolysin in the *B. thuringiensis* Al Hakam genome (Accession nos. CP000485 and CP000486) (3).

Example 2: Cloning, Expression and Purification of Putative Endolysins from the *B. cereus* E33L Genome The genes identified with the procedures illustrated in Example 1 were amplified from their respective genomes, cloned as described in Materials and Methods and expressed in a cell-free IVT system.

Figure 2:
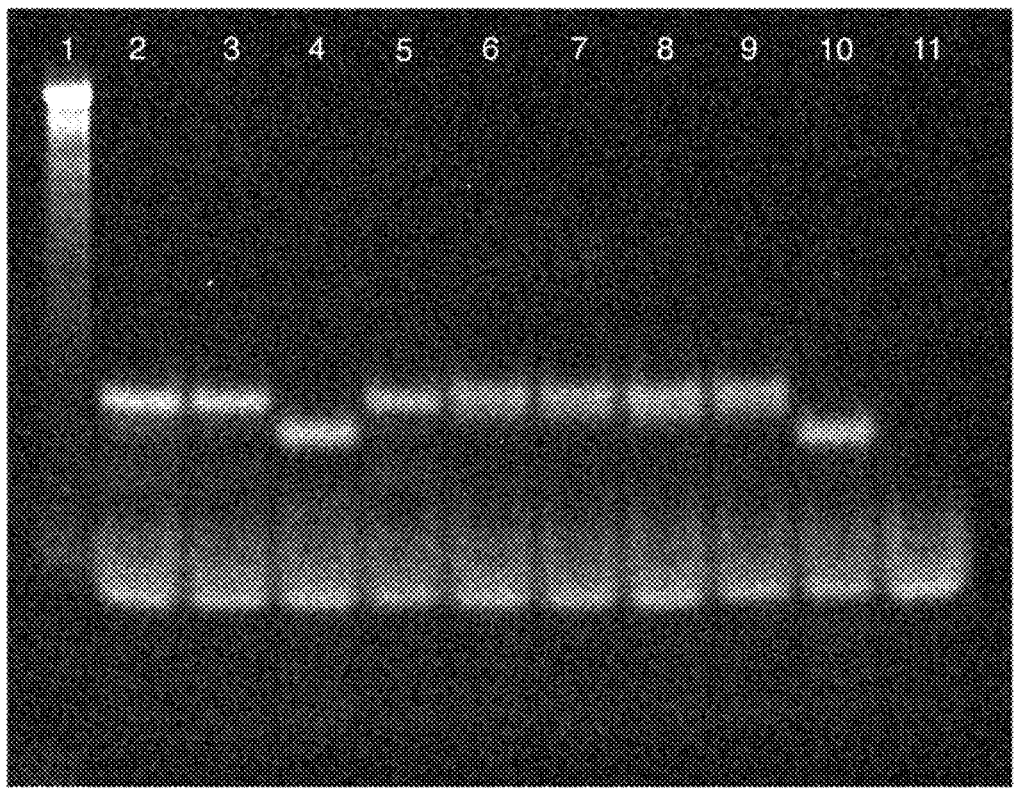

FIG. 2 shows the results of protein synthesis in IVT reactions labeled with the tRNA-Lysine-BODIPY conjugate FluoroTect GreenLys (Promega, Inc., Madison, Wis.). In particular FIG. 2 shows an analysis of IVT results expressing four different *Bacillus* endolytic proteins. Two clones each of four different genes encoding endolytic proteins were used to amplify the corresponding proteins in a cell-free IVT system labeled with BODIPY (1). Newly synthesized BODIPY-labeled proteins were separated by electrophoresis through a 4-12% polyacrylamide gel and the gel was scanned for BODIPY fluorescence. With the exception of one clone encoding the BA2446 (lane 5), all reactions generated proteins of the expected molecular weights.

The BCZK2532 endolysin (BCZK2532) was synthesized in an IVT reaction, purified through Nickel affinity columns and shown to be 93% pure based on LC-MS peptide sequencing (12).

Figure 3:
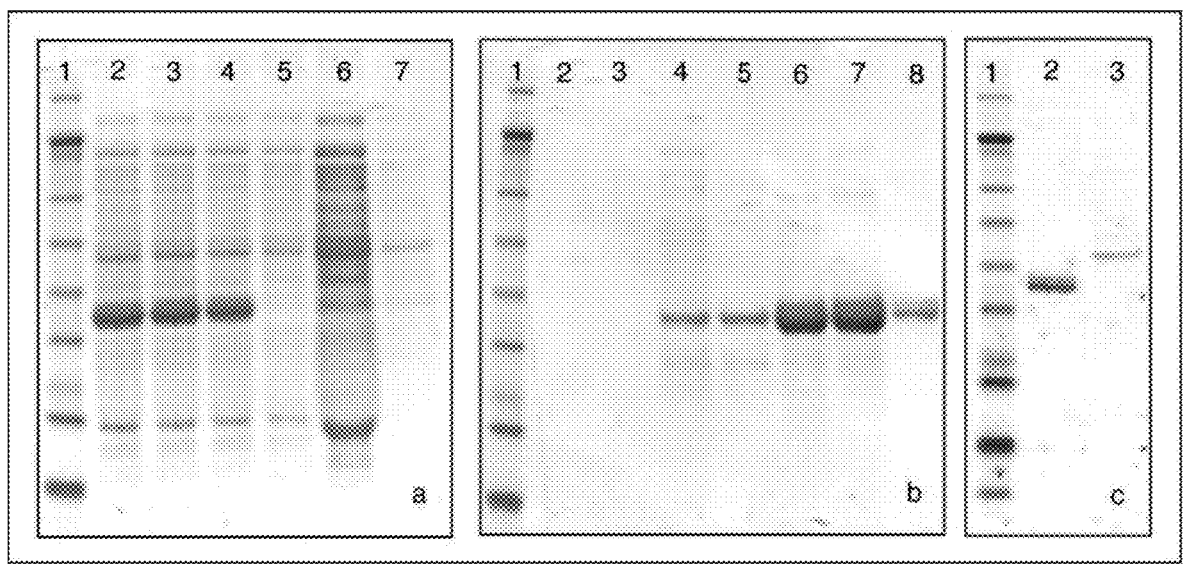

In particular, the results of the in vitro synthesis and purification of BCZK2532 endolysin are illustrated in FIG. 3. Two µg of purified pIVEX2.4d/BCZK2532 plasmid DNA, encoding the BCZK2532 containing a 6 residue Histidine tag was used to drive in vitro synthesis of the BCZK2532 endolytic enzyme using an RTS 500 ProteoMaster *E. coli* HY Kit (Roche Applied Science) (1). FIG. 3a shows a Coomassie Blue stained SDS-PAGE gel analysis of an IVT synthesis. Lane 1, molecular weight marker; lanes 2, 3 and 4, total proteins from WT reactions containing the pIVEX2.4d/BCZK2532 plasmid DNA; lane 5; results of flow-through upon loading a reaction on a Nickel-affinity column to purify the endolysin from other IVT components; lane 6, 0 mM imidazole wash 1; lane 7, 0 imidazole wash 2. FIG. 3b shows purification of the BCZK2532 from the Nickel-affinity column. Lane 1, molecular weight marker, lanes 2 through 5, 4 successive 10 mM imidazole washes; lanes 6 through 8, elution of purified endolysin from the column.

A 1 mL cell-free transcription-translation reaction generated 4 mg of affinity-purified protein. The calculated molecular weight of this His-tagged protein is 31.13 kDa. The apparent measured molecular weight, based on comparison to molecular weight standards on a polyacrylamide gel is 33 KDa.

This purified protein was used for the characterization studies. PlyL (BA4073), the prophage endolysin, was also expressed in the IVT system and purified to approximately 68% purity as determined by SDS-PAGE (FIG. 3c). This enzyme was previously purified to 90% purity after expression of the BA4073 gene in an *E. coli* in vivo expression system (20).

Example 3: Testing Antimicrobial Activity of BCZK2532-on *B. anthracis* Sterne

Nickel-affinity purified proteins obtained with the procedure exemplified in Example 2 were then assayed for activity on a lawn of *B. anthracis* Sterne cells.

Figure 4:
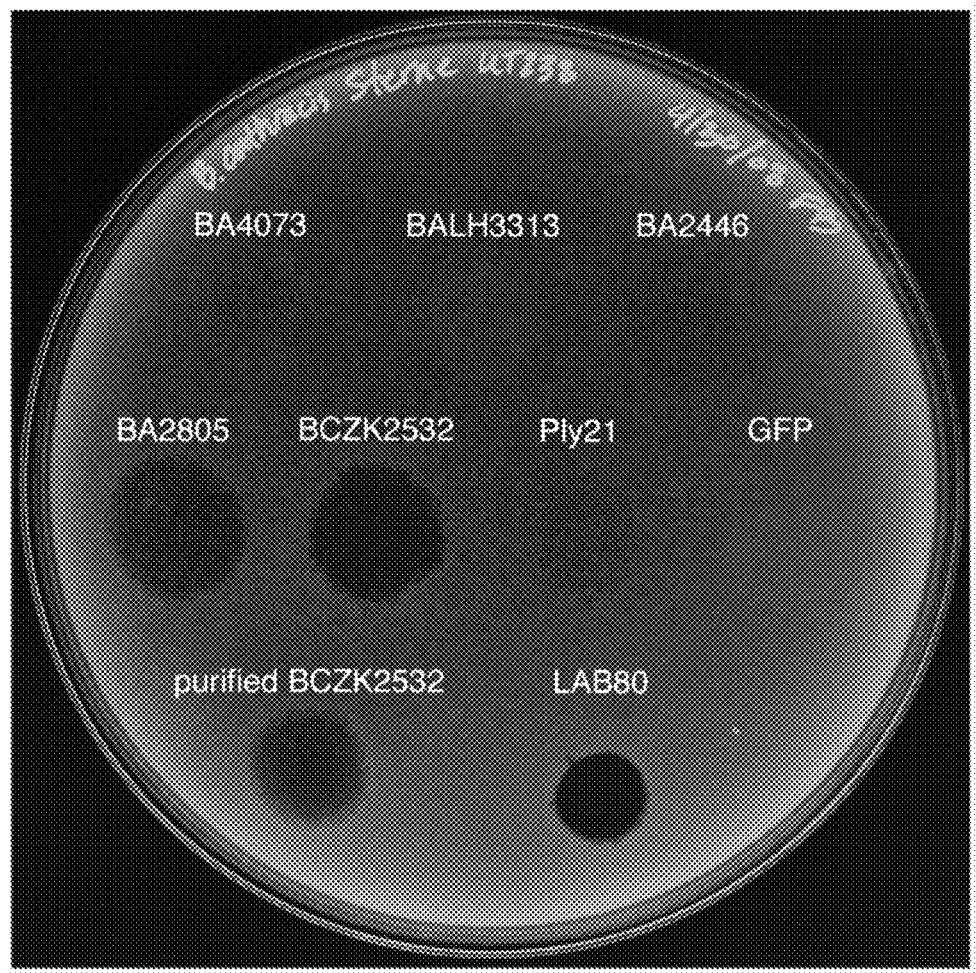

FIG. 4 shows the results of the related endolysin spot tests. Nickel affinity column-purified endolysin preparations were tested by placing each purified protein on a freshly plated suspension of *B. anthracis* Sterne cells. Five minutes after plating the bacterial cells, 10 µl of each protein was spotted onto the plate and the plate was incubated overnight at 35° C. overnight. The following day, spots were assayed for evidence of bacterial lysis. Each spot is labeled with the protein deposited on that spot. Ten µl of IVT synthesized green fluorescent protein (GFP) was spotted on the plate as a negative control and 10 µl of bacteriophage LAB80, a bacteriophage that infects *B. anthracis*, was spotted as a positive control.

In the illustration of FIG. 4, endolysins encoded by BA4073 and BA2446 (spots 1 and 3) showed very limited lytic activity. The endolysin encoded by BALH_3313 from *B. thuringiensis* Al Hakam showed no measurable activity. The endolysins encoded by two almost identical genes, BA2805 and BCZK2532, showed significant activity compared to a highly purified preparation of the BCZK2532 enzyme. As expected, IVT-produced GFP had no affect on the cultures. *Bacillus* bacteriophage LAB80, a soil isolate previously shown to infect *B. anthracis*, was included as a positive control and cleared the bacterial lawn as expected. The endolysin encoded by BCZK2532 showed the highest level of activity and was selected for further analysis.

Example 4: BCZK2532-Mediated Lysis of *B. anthracis* Sterne

*B. anthracis* Sterne cells expressing GFP were grown and prepared as described above. One culture was divided into five aliquots and differing concentrations of BCZK2532 endolysin were added to each aliquot. In particular, purified BCZK2532 was diluted three orders of magnitude and tested for specific activity using a *B. anthracis* Sterne isolate (7702) containing a GFP-encoding plasmid (pUTE610) (22). Analysis of the results used flow cytometry to monitor the change in cell fluorescence with exposure to the endolysin and culture plating to measure the impact of endolysin activity on survival of the culture.

The results are shown in FIG. 5 which illustrate flow cytometric analysis of the lysis of *B. anthracis* Sterne cells expressing the Green Fluorescent Protein (GFP) with BCZK2532.

Greater that 90% of the *B. anthracis* cells were impacted by exposure to 1 nM (33 ng/ml) BCZK2532 for 60 minutes at 30° C. (FIG. 5a). Exposure to 50 nM protein impacted greater than 99% of the cells. Exposure to 1 nM BCZK2532 for 10 minutes at 30° C. resulted in significantly less than 10% survival of the cells in the culture as determined by the number of CFU and exposure to as little as 10 nM for as little as 10 minutes resulted in significantly less than 1% survival (FIG. 5b). The viability curves shown in FIG. 5b closely matched the flow cytometry results.

Figure 6:
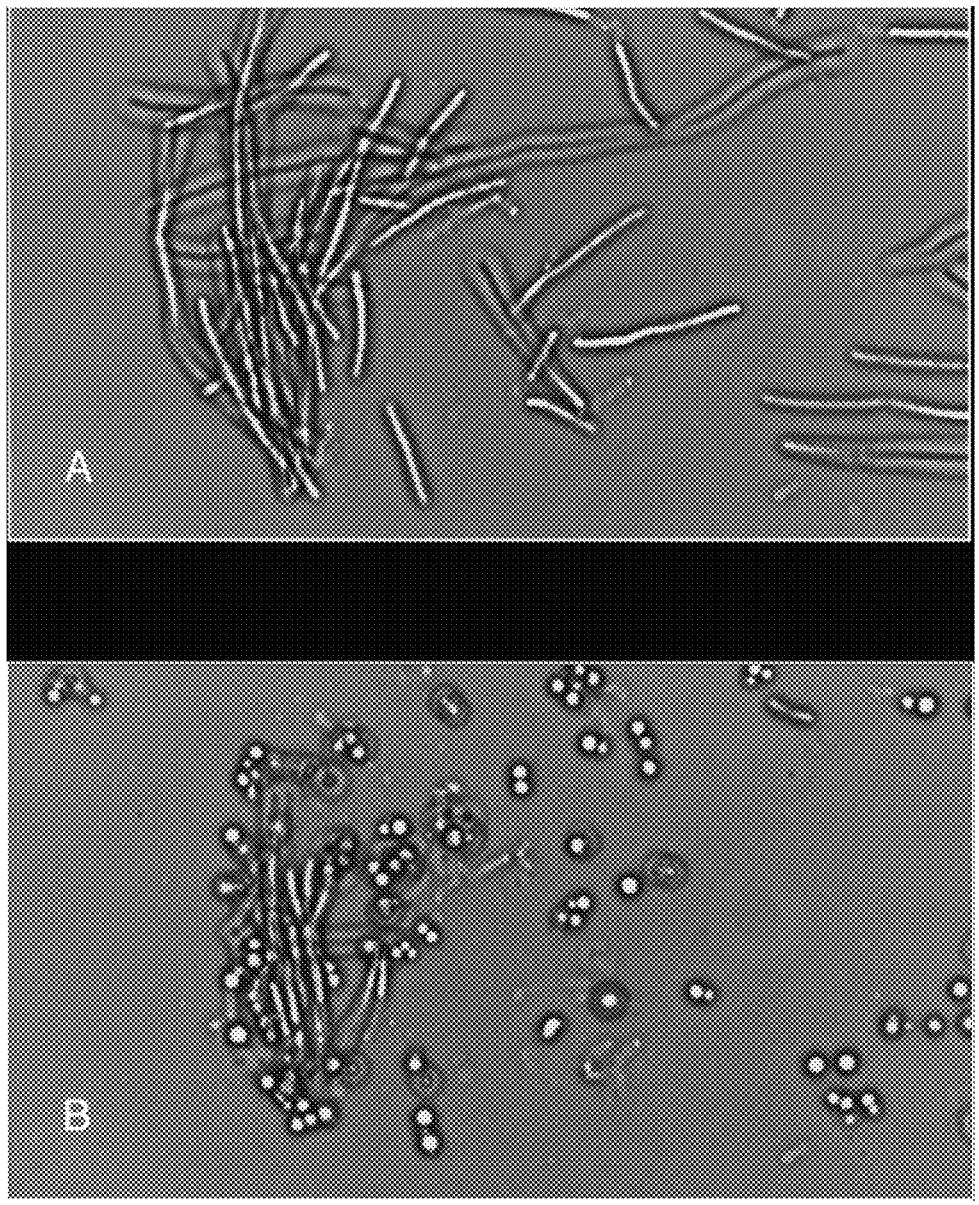

FIG. 6 shows a microscopic visualization of BCZK2532 endolysin treatment. Micrographs of *B. anthracis* Sterne cells after exposure to 2.5 µg/mL for 0 minutes (FIG. 6A) and after 3 minutes of exposure (Panel 6B). Both images, frames taken from a movie of cell lysis, are of the same microscopic field before and after treatment with the endolysin.

The change in cell morphology from chains of *B. anthracis* cells to a spherical shape is consistent with destruction of the bacterial cell wall. Such cells are not viable as measured by culturing and plating methods.

Example 5: BCZK2532 Protein Stability and Enzyme Properties

A Nickel-column purified BCZK2532 was stored at 4° C. in 1× protein storage buffer and tested by polyacrylamide gel electrophoresis and by measuring *B. anthracis* lytic activity at different times over eight months. There was no detectible protein degradation or loss of endolytic activity following eight months of protein storage at 4° C. (data not shown).

The BZCK2532 lytic protein has significantly increased lytic activity, as measured by the number of cells killed by a specific concentration of this protein used to treat a specific number of cells at a specific temperature for a specific period of time, relative to the phage endolytic proteins and other lytic proteins so far tested. One or more factors such as protein solubility, enzyme turnover rates and the number of times an enzyme molecule can catalyze a particular reaction before in no longer functions, are expected to influence measured activity.

Example 6: Specificity of BCZK2532 for Different *Bacillus* Species

BCZK2532 was applied to very close relatives of *B. anthracis* to understand the range of different closely related species and strains that this lytic protein could impact. In addition to testing against *B. anthracis* and *B. cereus* E33L, the ability to lyse *B. thuringiensis* 97-27, *B. thuringiensis* HD1, *B. thuringiensis* HD560 and *B. thuringiensis* HD658 was also tested.

*B. thuringiensis* serovar *konkukian* 97-27 is a very unusual *B. thuringiensis* isolate. It is a close relative of *B. anthracis* isolated from a severely infected wound of a French soldier and shown to be infectious in animal models (7). In contrast, *B. thuringiensis* serovar *kurstaki* HD1, serovar israelensis HD560 and serovar kenyae are all used to control insects and are not very closely related to *B. anthracis* phylogenetically (8).

Six different *Bacillus* isolates were treated with 100 nM BCZK2532 or Ply21 endolysin for 1 hour, then cells were plated at different dilutions on nutrient broth plates, and incubated overnight to determine the number of surviving cells. Cells treated with BCZK2532 are labeled in black and cells treated with Ply21 are labeled in gray. The results shown in FIG. 7 are from two different plating experiments. Results are plotted as percent survival compared to untreated cells.

BCZK2532 showed lytic activity at a concentration of 100 nM against all of the *Bacillus* isolates tested based on a reduction in CFU of cultures exposed when cells were treated for 1 hour (FIG. 7). However, it is much more effective against *B. anthracis* and *B. cereus* E33L than it is against the *B. thuringiensis* isolates. Only 0.1% of the *B. anthracis* Sterne and 3.7% of the *B. cereus* E33L survived this treatment. It is not surprising that this lytic protein has similar activities against these two pathogens because, while the gene sequence differs by less than 1% (six point mutations), only one of the six point mutations results in a change in an amino acid. Only 3.1% of the *B. thuringiensis* serovar *konkukian* 97-27 survived this treatment.

In contrast, 15% of the treated *B. thuringiensis* serovar israelensis HD658 cells, 40% of the *B. thuringiensis* serovar kenyae HD560 cells and 48% of the *B. thuringiensis* serovar *kurstaki* HD1 survived exposure to the endolysin. There appears to be some correlation between the phylogenetic distance of the *B. thuringiensis* isolate (*B. thuringiensis konkukian* 97-27 is a close relative of *B. anthracis* while the other *B. thuringiensis* isolates are only distantly related) but there is no direct correlation between the efficacy of this endolysin and the phylogenetic distance of the treated cells from *B. cereus* E33L. The Ply21 endolysin used in these experiments was expressed from the genome of the bacteriophage TP-21-L, a known *B. anthracis* phage. It is therefore surprising that this endolysin shows less lytic activity against *B. anthracis* and *B. cereus* (E33L) than it does against all but one of the *B. thuringiensis* isolates. However, none of the other *B. thuringiensis* strains have been tested as hosts for this phage.

In view of the above, it would be apparent to a skilled person that nanomolar concentrations of in vitro expressed, purified BCZK2532 endolysin cause rapid, complete lysis of *B. anthracis* and *B. cereus* E33L cells. Very low concentrations of this protein (2.5 µg/mL) can completely lyse a *B. anthracis* Sterne culture containing approximately $5 \times 10^8$ cells/mL in several minutes (FIGS. 7a and b). The BCZK2532 gene sequence is greater than 99% similar to a homologous gene in *B. anthracis*. There are six nucleotide differences between the *B. anthracis* and *B. cereus* E33L (BCZK2532) gene sequences. However, five of these differences are synonymous, leading to no differences in the amino acid sequences of the two proteins. The sixth difference at position 100, results in an arginine to isoleucine substitution. BCZK2532 has slightly lower lytic activity against *B. anthracis* relative to *B. cereus* E33L (data not shown). This amino acid residue may have some importance in catalytic activity because it maps to the catalytic domain of this protein (18), however there is no known reason why this change in protein sequences would cause a difference in lytic activity between the two bacterial isolates. It may be that there are differences in the *B. anthracis* cell wall relative to *B. cereus* E33L that are responsible for this effect.

In view of the above data, it is also possible to conclude that BCZK2532 is not absolutely specific for its host and *B. anthracis* but has a relatively narrow range of activity against other *Bacillus* isolates, at least at the very low concentrations that are effective against *B. anthracis* and *B. cereus* E33L. The BCZK2532 catalytic activity is significantly greater than that of comparable *Bacillus* phage-derived endolysins. The bacteriophage endolysin PlyL will lyse a *B. anthracis* culture ($5 \times 10^8$ cells/mL in exponential phase) within 10 minutes at 2 µM concentrations (20). The PlyB bacteriophage endolysin will lyse a similar culture of *B. cereus* ATCC 4342 cells in 10 minutes at 625 nM concentrations. The BCZK2532 endolytic protein will lyse a *B. anthracis* Sterne culture in 10 minutes at 10 nM concentrations.

This endolysin is a very stable protein. Purified preparations were stored at 4° C. with no special protection for at least eight months without loss of activity. Moreover, the protein does not appear to be degraded when added to cultured cells, suggesting that it is relatively resistant to the proteases and other components found in a bacterial cell culture.

The cell-free in vitro translation used in the above experiments produced a recombinant, easily purified protein with very high lytic activity. A single IVT reaction produced 6 mg of purified protein. The approach provided significantly better results than those obtained by using a traditional *E. coli* protein expression system. The latter method produced some active lytic protein but generated large amounts of insoluble protein with very low specific activity. The IVT approach coupled with single-step affinity chromatography allowed synthesis and purification of large, high quality protein preparations in a relatively short time period. Optimization of the expression of such proteins in a cell-based system is expected to be useful, in particular for therapeutic applications. However, for initial testing and characterization of such proteins, the IVT-based methods have significant advantages.

A survey of all the available sequenced bacterial pathogens genomes reveals that all the genomes available carry one or more genes encoding endolytic proteins similar to those involved in bacteriophage-mediated bacterial cell lysis. *B. cereus* E33L contains several other genes encoding potential lytic proteins besides those described here. These proteins have been implicated in cell wall metabolism and, as such, may be required for cell wall synthesis, recycling and maintenance (10, 11, 17). If they fulfill a required need in cell metabolism, then it is unlikely that the microbes from which they were derived will develop mechanisms of resistance to these lytic agents. It is therefore not necessary to mine bacteriophage genomes for genes encoding these potentially antimicrobial proteins. Instead, one can identify these sequences in the bacterial genomes. Then it is simply a matter of designing the appropriate primers to amplify the gene from a very small amount of pathogen DNA and cloning and expressing the gene to produce a potential antimicrobial protein. Rapid genomic sequencing of newly identified pathogens will facilitate identification of genes encoding such proteins in these newly identified microbes. Many bacterial genomes contain prophage sequences, another potential source of genes encoding lytic proteins.

Information about crucial microbial metabolic pathways has long been used as a means to identify potential antimicrobial agents that severely impact the growth and reproduction of bacterial pathogens. The results presented here suggest that DNA sequences mined from available pathogenic microbial genome sequences can themselves be used directly in strategies to control or destroy these pathogens.

Example 7: Exemplary Procedure for Identifying a Targeted Antimicrobial in a Microorganism The following exemplary procedure has been developed on the basis of the experiments and research exemplified above and is expected to be suitable to provide efficient selection for any microorganism herein described.

Identify gene sequence to be cloned and develop a restriction enzyme or polymerase chain reaction (PCR) based cloning strategy. Protein identification for novel protein sequences can be based on local protein or DNA alignment studies that compare relatedness (identity and similarity) using a known sequence, or compilation of sequences, to search any available database that contains genetic (DNA) or protein sequences or information. Proteins with a BLAST "Total Score" of or above 100 or corresponding homology can be selected.

Clone gene sequence into an appropriate commercially available T7 polymerase driven cloning vector such as the pIVEX 2.4b Nde vector. Alternatively or in concert with traditional vector-based cloning strategies, attach or engineer T7-promoter and T7-terminator sequences into a PCR product (DNA) that contains the gene of interest for use as a template during protein expression. Include DNA sequences encoding an affinity tag in the sequence of interest for subsequent protein purification. Cloning vectors such as pIVEX-MBP or pIVEX-GST could also be used to increase expression and/or proper folding. This approach can be particularly desired for proteins that do not fold into active structures on their own.

Purify and quantitate the DNA template(s) to be used to produce protein(s) by standard, commercially available methods or by traditional DNA precipitation approaches (i.e. ammonium acetate precipitation). Quantitation technologies may include gel electrophoresis and spectrophotometric or chemical dye incorporation and UV detection.

Use a commercial in vitro translation protein expression system (Cell-free expression) or kit (such as the 5 Prime RTS 100 *E. coli* HY Kit) to express the gene of interest as a protein. These kits produce functionally active proteins from both circular (plasmid) and linear (PCR product) DNA templates.

Purify the protein using the appropriate affinity matrix (tag dependent) and determine the yield, purity, solubility and stability using common laboratory protein purification and analytical methods (Bradford analysis, PAGE, dialysis and buffer exchange, storage at differing temperatures with and without stabilizers such as glycerol, bovine serum albumin, etc.). Solubility issues can be alleviated by adding detergents to the in vitro translation reaction, listed in Schwarz, D. et al., 2007 "Preparative scale cell-free expression systems: New tools for the large scale preparation of integral membrane proteins for functional and structural studies," Methods 41:4.

Add a known amount of purified protein to a Petri dish that contains the bacterial strain in a double-agar overlay (top agar method). Add the protein droplet-wise in a volume of one to five microliters. Allow the spot to absorb into the top agar surface. Incubate overnight under conditions suitable for the growth of the bacterial sample being tested against.

For proteins that are lytic (targeted antimicrobials that inactivate bacterial cells), continue to characterize the activity of the protein by standard biochemical methods.

In general the strategy developed by Applicants is to mine microorganism genome information to identify proteins that, when expressed inappropriately or when used to drive synthesis of large amounts of a particular product, can result in the production of antimicrobial compounds effective against the pathogenic microbe in which the gene was identified or genetically related microbes. This approach significantly differs from the usual strategy to identify required bacterial processes then producing antimicrobial compounds that interfere with these processes. Muramidases are only one example of a class of bacterial proteins that appear to function in cell wall biosynthesis and metabolism. A good number of genes encoding muramidases proteins were first identified in mutation studies that showed that changes in the genes or their expression resulting in changes in cell wall metabolism. Additional lytic proteins are also comprised as long as they target and/or inactivate and possibly destroy specific moieties in a specific target organism's cell wall, which in certain conditions cause the targeted microorganism to lyse or burst. Empirical data suggest that some lytic enzymes are more stable and more active than others. There are four known examples of this class of proteins; muramidases, amidases, endopeptidases, and L-alanyl-D-glutamate peptidases; and others are expected to be comprised based on the current understanding of bacterial cell wall metabolism.

Example 8: Exemplary Procedure for Identifying a Candidate Antimicrobial in a Microorganism The NCBI database was searched based on annotation. The following list of putative *Yersinia pestis* endolysins reported in Table 3 was identified using "*Yersinia*" and "amidase" as search terms. These genes were not chosen based on a single phage sequence, but chosen based on simple annotation in the database.

TABLE 3

| Entry | Pfam |
|---|---|
| YPO0370 | Amidase_3 OmpA LysM |
| YPO1023 | Amidase_3 |
| YPO1683 | Amidase_2 PG_binding_1 |
| YPO1715 | Amidase_2 PG_binding_1 |
| y0627 | Amidase_3 OmpA LysM |
| y1845 | Amidase_2 PG_binding_1 |
| y1877 | Amidase_2 PG_binding_1 |
| y3161 | Amidase_3 |
| y0763 | N-acetyl-anhydromuranmyl-L-alanine amidase |
| YPTB0422 | Amidase_3 OmpA LysM |
| YPTB2366 | Amidase_2 PG_binding_1 |
| YPTB2395 | Amidase_2 PG_binding_1 |
| YPTB3022 | Amidase_3 |
| YP_0526 | Amidase_3 OmpA LysM |
| YP_1740 | Amidase_2 PG_binding_1 |
| YP_1812 | Amidase_2 PG_binding_1 |
| YP_2827 | Amidase_3 |
| YPA_0495 | Amidase_3 |
| YPA_1806 | Amidase_2 PG_binding_1 |
| YPA_1839 | Amidase_2 PG_binding_1 |
| YPA_3914 | Amidase_3 OmpA LysM |
| YPN_1915 | Amidase_2 PG_binding_1 |
| YPN_1948 | Amidase_2 PG_binding_1 |
| YPN_2978 | Amidase_3 |
| YPN_3301 | Amidase_3 OmpA LysM |
| YPDSF_1689 | Amidase_3 |
| YPDSF_1733 | Amidase_2 PG_binding_1 |
| YPDSF_1765 | Amidase_2 PG_binding_1 |
| YPDSF_3604 | Amidase_3 OmpA LysM |

TABLE 3-continued

| Entry | Pfam |
|---|---|
| YpAngola_A0702 | Amidase_3 OmpA LysM |
| YpAngola_A2652 | Amidase_2 PG_binding_1 |
| YpAngola_A3228 | Amidase_3 |
| YpAngola_A3523 | Amidase_2 PG_binding_1 |

A possible approach is to proceed and test the protein of Table 3 for antimicrobial activity. Another possible approach could be that of performing an additional search looking for genes identified as playing a role in cell wall synthesis, which is expected to identify a second set of genes encoding candidate lytic proteins and/or a third search directed to target some other subset of genes encoding proteins with known lytic function.

The proteins selected according to the procedures are then tested for antimicrobial activity according to methods herein described.

Example 9: Exemplary Procedure for Identifying a Candidate Antimicrobial in a Microorganism NCBI database was searched using BLAST.
The query sequence used is from known *Staphylococcus* phage Twort endolysin is the following
LOCUS CAA69021 467 aa linear PHG 26 May 1999
DEFINITION N-acetylmuramoyl-L-alanine amidase [*Staphylococcus* phage Twort].
ACCESSION CAA69021
VERSION CAA69021.1 gi:2764981
SOURCE *Staphylococcus* phage Twort
Exemplary sequences retrieved and showing significant alignment are reported in Table 4 below

TABLE 4

Exemplary sequences producing significant alignments:

| Accession | Description | Max score | Total score | Query coverage | Value |
|---|---|---|---|---|---|
| CBI48272.1 | autolysin; hypothetical phage protein [*Staphylococcus aureus* subsp. *aureus* TW20] | 341 | 341 | 99% | 6e-94 |
| NP_371437.1 | amidase [*Staphylococcus aureus* subsp. *aureus* Mu50] >ref|YP_001441498.1|amidase [*Staphylococcus aureus* subsp. *aureus* Mu3] >ref|ZP_05144303.2|amidase [*Staphylococcus aureus* subsp. *aureus* Mu50-omega] >dbj|BAB57075.1|amidase [*Staphylococcus aureus* subsp. *aureus* Mu50] >dbj|BAF77791.1|amidase [*Staphylococcus aureus* subsp. *aureus* Mu3] | 340 | 340 | 99% | 1e-93 |
| ZP_04840302.1 | amidase [*Staphylococcus aureus* subsp. *aureus* str. CF-Marseille] | 339 | 339 | 99% | 1e-93 |
| ZP_03562550.1 | autolysin [*Staphylococcus aureus* subsp. *aureus* str. JKD6008] >ref|ZP_03566881.1|autolysin [*Staphylococcus aureus* subsp. *aureus* str. JKD6009] | 337 | 337 | 99% | 6e-93 |
| ZP_06948777.1 | N-acetylmuramoyl-L-alanine amidase [*Staphylococcus aureus* subsp. *aureus* MN8] >gb|EFH95979.1|N-acetylmuramoyl-L-alanine amidase [*Staphylococcus aureus* subsp. *aureus* MN8] | 337 | 337 | 99% | 6e-93 |
| ZP_06327377.1 | N-acetylmuramoyl-L-alanine amidase [*Staphylococcus aureus* subsp. *aureus* C427] >gb|EFB46660.1|N-acetylmuramoyl-L-alanine amidase [*Staphylococcus aureus* subsp. *aureus* C427] | 336 | 336 | 99% | 1e-92 |
| ZP_05693156.1 | N-acetylmuramoyl-L-alanine amidase [*Staphylococcus aureus* A6300] >ref|ZP_05696133.1|N-acetylmuramoyl-L-alanine amidase [*Staphylococcus aureus* A6224] >gb|EEV79067.1|N-acetylmuramoyl-L-alanine amidase [*Staphylococcus aureus* A6300] >gb|EEV81611.1|N-acetylmuramoyl-L-alanine amidase [*Staphylococcus aureus* A6224] | 336 | 336 | 99% | 2e-92 |
| YP_001332073.1 | phage amidase [*Staphylococcus aureus* subsp. *aureus* str. Newman] >dbj|BAF67311.1|phage amidase [Bacteriophage phiNM2] [*Staphylococcus aureus* subsp. *aureus* str. Newman] | 336 | 336 | 99% | 2e-92 |

TABLE 4-continued

Exemplary sequences producing significant alignments:

| Accession | Description | Max score | Total score | Query coverage | Value |
|---|---|---|---|---|---|
| YP_001245749.1 | N-acetylmuramoyl-L-alanine amidase [*Staphylococcus aureus* subsp. *aureus* JH9] >ref|YP_001315525.1|N-acetylmuramoyl-L-alanine amidase [*Staphylococcus aureus* subsp. *aureus* JH1] >gb|ABQ48173.1|N-acetylmuramoyl-L-alanine amidase [*Staphylococcus aureus* subsp. *aureus* JH9] >gb|ABR51238.1|N-acetylmuramoyl-L-alanine amidase [*Staphylococcus aureus* subsp. *aureus* JH1] | 336 | 336 | 99% | 2e-92 |
| ZP_06930705.1 | N-acetylmuramoyl-L-alanine amidase [*Staphylococcus aureus* A8796] >gb|EFH35527.1|N-acetylmuramoyl-L-alanine amidase [*Staphylococcus aureus* A8796] | 336 | 336 | 99% | 2e-92 |
| ZP_06327634.1 | N-acetylmuramoyl-L-alanine amidase [*Staphylococcus aureus* A9765] >gb|EFB99605.1|N-acetylmuramoyl-L-alanine amidase [*Staphylococcus aureus* A9765] | 336 | 336 | 99% | 2e-92 |
| YP_500516.1 | autolysin [*Staphylococcus aureus* subsp. *aureus* NCTC 8325] >gb|ABD31075.1|autolysin [*Staphylococcus aureus* subsp. *aureus* NCTC 8325] | 335 | 335 | 97% | 2e-92 |
| ZP_06343855.1 | N-acetylmuramoyl-L-alanine amidase [*Staphylococcus aureus* subsp. *aureus* H19] >gb|EFC06649.1|N-acetylmuramoyl-L-alanine amidase [*Staphylococcus aureus* subsp. *aureus* H19] | 334 | 334 | 99% | 5e-92 |
| ZP_05687279.1 | phage amidase [*Staphylococcus aureus* A9635] >gb|EEV69446.1|phage amidase [*Staphylococcus aureus* A9635] | 334 | 334 | 99% | 5e-92 |
| YP_417165.1 | phage-related amidase [Staphylococcus aureus RF122] >emb|CAI81392.1|phage-related amidase [*Staphylococcus aureus* RF122] | 334 | 334 | 99% | 6e-92 |
| ZP_06324909.1 | N-acetylmuramoyl-L-alanine amidase [*Staphylococcus aureus* subsp. *aureus* D139] >gb|EFB49136.1|N-acetylmuramoyl-L-alanine amidase [*Staphylococcus aureus* subsp. *aureus* D139] | 333 | 333 | 99% | 1e-91 |
| YP_001246457.1 | N-acetylmuramoyl-L-alanine amidase [*Staphylococcus aureus* subsp. *aureus* JH9] >ref|YP_001316244.1|N-acetylmuramoyl-L-alanine amidase [*Staphylococcus aureus* subsp. *aureus* JH1] >gb|ABQ48881.1|N-acetylmuramoyl-L-alanine amidase [*Staphylococcus aureus* subsp. *aureus* JH9] >gb|ABR51957.1|N-acetylmuramoyl-L-alanine amidase [*Staphylococcus aureus* subsp. *aureus* JH1] | 333 | 333 | 99% | 1e-91 |
| ZP_05684021.1 | amidase [*Staphylococcus aureus* A9719] >gb|EEV67324.1| amidase [*Staphylococcus aureus* A9719] | 332 | 332 | 99% | 2e-91 |
| ZP_05642208.1 | amidase [*Staphylococcus aureus* A9781] >gb|EEV25541.1| amidase [*Staphylococcus aureus* A9781] | 332 | 332 | 99% | 2e-91 |
| CAQ49916.1 | autolysin (N-acetylmuramoyl-L-alanine amidase) [*Staphylococcus aureus* subsp. *aureus* ST398] | 332 | 332 | 99% | 2e-91 |
| P24556.1 | RecName: Full = Autolysin; AltName: Full = N-acetylmuramoyl-L-alanine amidase | 316 | 316 | 99% | 2e-86 |
| ADI97637.1 | Phage amidase [*Staphylococcus aureus* subsp. *aureus* ED133] | 169 | 169 | 43% | 3e-42 |
| ZP_06859751.1 | autolysin [*Staphylococcus aureus* subsp. *aureus* MR1] | 142 | 142 | 53% | 3e-34 |
| NP_646703.1 | lytic enzyme [*Staphylococcus aureus* subsp. *aureus* MW2] >ref|YP_041411.1|autolysin [*Staphylococcus aureus* subsp. *aureus* MRSA252] >ref|YP_494574.1|autolysin [*Staphylococcus aureus* subsp. *aureus* USA300_FPR3757] >ref|YP_500659.1|amidase [*Staphylococcus aureus* subsp. *aureus* NCTC 8325] >ref|YP_001247363.1|CHAP domain-containing protein [*Staphylococcus aureus* subsp. *aureus* JH9] >ref|YP_001317155.1|CHAP domain-containing protein [*Staphylococcus aureus* subsp. *aureus* JH1] >ref|YP_001332915.1|phage amidase [*Staphylococcus aureus* subsp. *aureus* str. Newman] >ref|YP_001575829.1|N-acetylmuramoyl-L-alanine amidase [*Staphylococcus aureus* subsp. *aureus* USA300_TCH1516] >ref|ZP_03564467.1|N-acetylmuramoyl-L-alanine amidase [*Staphylococcus aureus* subsp. *aureus* str. JKD6008] >ref|ZP_03564829.1|N-acetylmuramoyl-L-alanine amidase [*Staphylococcus aureus* subsp. *aureus* str. JKD6009] >ref|ZP_04015764.1|N-acetylmuramoyl-L-alanine amidase [*Staphylococcus aureus* subsp. *aureus* TCH60] >ref|ZP_04863892.1|N-acetylmuramoyl-L-alanine amidase [*Staphylococcus aureus* subsp. *aureus* USA300_TCH959] >ref|ZP_04869096.1|N-acetylmuramoyl-L-alanine amidase [*Staphylococcus aureus* subsp. *aureus* TCH130] >ref|ZP_05602501.1|lytic enzyme [*Staphylococcus aureus* subsp. *aureus* 55/2053] >ref|ZP_05605147.1|autolysin [*Staphylococcus aureus* subsp. *aureus* 65-1322] >ref|ZP_05607737.1|autolysin [*Staphylococcus aureus* subsp. *aureus* 68-397] >ref|ZP_05610430.1|lytic enzyme [*Staphylococcus aureus* | 142 | 142 | 53% | 3e-34 |

TABLE 4-continued

Exemplary sequences producing significant alignments:

| Accession | Description | Max score | Total score | Query coverage | Value |
|---|---|---|---|---|---|
| | subsp. *aureus* E1410] >ref|ZP_05613027.1|phage amidase [*Staphylococcus aureus* subsp. *aureus* M876] >ref|ZP_05642310.1|lytic enzyme [*Staphylococcus aureus* A9781] >ref|ZP_05683989.1|amidase [*Staphylococcus aureus* A9719] >ref|ZP_05685925.1|amidase [*Staphylococcus aureus* A9635] >ref|ZP_05688345.1| autolysin [*Staphylococcus aureus* A9299] >ref|ZP_05691059.1|phage amidase [*Staphylococcus aureus* A8115] >ref|ZP_05698717.1|lytic enzyme [*Staphylococcus aureus* A5948] >ref|ZP_06302943.1|N-acetylmuramoyl-L-alanine amidase [*Staphylococcus aureus* A8117] >ref|ZP_06312466.1|gametolysin [*Staphylococcus aureus* subsp. *aureus* C160] >ref|ZP_06313693.1|N-acetylmuramoyl-L-alanine amidase [*Staphylococcus aureus* subsp. *aureus* Btn1260] >ref|ZP_06317082.1|phage amidase [*Staphylococcus aureus* subsp. *aureus* WW2703/97] >ref|ZP_06319373.1|phage amidase [*Staphylococcus aureus* subsp. *aureus* WBG10049] >ref|ZP_06322531.1|gametolysin [*Staphylococcus aureus* subsp. *aureus* M899] >ref|ZP_06325048.1|N-acetylmuramoyl-L-alanine amidase [*Staphylococcus aureus* subsp. *aureus* D139] >ref|ZP_06327594.1|N-acetylmuramoyl-L-alanine amidase [*Staphylococcus aureus* subsp. *aureus* C427] >ref|ZP_06332848.1|N-acetylmuramoyl-L-alanine amidase [*Staphylococcus aureus* subsp. *aureus* C101] >ref|ZP_06333733.1|N-acetylmuramoyl-L-alanine amidase [*Staphylococcus aureus* A9765] >ref|ZP_06379390.1| autolysin [*Staphylococcus aureus* subsp. *aureus* 132] >ref|ZP_06667664.1|N-acetylmuramoyl-L-alanine amidase [*Staphylococcus aureus* subsp. *aureus* 58-424] >ref|ZP_06669030.1|phage amidase [*Staphylococcus aureus* subsp. *aureus* M809] >ref|ZP_06672059.1|gametolysin [*Staphylococcus aureus* subsp. *aureus* M1015] >ref|ZP_06790239.1|N-acetylmuramoyl-L-alanine amidase [*Staphylococcus aureus* A9754] >ref|ZP_06817250.1|N-acetylmuramoyl-L-alanine amidase [*Staphylococcus aureus* A8819] >ref|ZP_06821156.1|autolysin [*Staphylococcus aureus* subsp. *aureus* EMRSA16] >ref|ZP_06925225.1|N-acetylmuramoyl-L-alanine amidase [*Staphylococcus aureus* subsp. *aureus* ATCC 51811] >ref|ZP_06930164.1|N-acetylmuramoyl-L-alanine amidase [*Staphylococcus aureus* A8796] >ref|ZP_06948638.1|N-acetylmuramoyl-L-alanine amidase [*Staphylococcus aureus* subsp. *aureus* MN8] >dbj|BAB95751.1|lytic enzyme [*Staphylococcus aureus* subsp. *aureus* MW2] >emb|CAG41025.1|autolysin [*Staphylococcus aureus* subsp. *aureus* MRSA252] >gb|ABD20608.1|autolysin [*Staphylococcus aureus* subsp. aureus USA300_FPR3757] >gb|ABD31217.1|amidase [*Staphylococcus aureus* subsp. *aureus* NCTC 8325] >gb|ABQ49787.1|CHAP domain containing protein [*Staphylococcus aureus* subsp. *aureus* JH9] >gb|ABR52868.1| CHAP domain containing protein [*Staphylococcus aureus* subsp. *aureus* JH1] >dbj|BAF68153.1|phage amidase [*Staphylococcus aureus* subsp. *aureus* str. Newman] >gb|ABX29950.1|N-acetylmuramoyl-L-alanine amidase [*Staphylococcus aureus* subsp. *aureus* USA300_TCH1516] >gb|EEJ63599.1|N-acetylmuramoyl-L-alanine amidase [*Staphylococcus aureus* subsp. *aureus* TCH60] >gb|EES95264.1|N-acetylmuramoyl-L-alanine amidase [*Staphylococcus aureus* subsp. *aureus* USA300_TCH959] >gb|EES95842.1|N-acetylmuramoyl-L-alanine amidase [*Staphylococcus aureus* subsp. *aureus* TCH130] >gb|EEV03379.1|lytic enzyme [*Staphylococcus aureus* subsp. *aureus* 55/2053] >gb|EEV05908.1|autolysin [*Staphylococcus aureus* subsp. *aureus* 65-1322] >gb|EEV08666.1|autolysin [*Staphylococcus aureus* subsp. aureus 68-397] >gb|EEV11149.1|lytic enzyme [*Staphylococcus aureus* subsp. *aureus* E1410] >gb|EEV13899.1|phage amidase [*Staphylococcus aureus* subsp. *aureus* M876] >gb|EEV25643.1|lytic enzyme [*Staphylococcus aureus* A9781] >gb|EEV67424.1|amidase [*Staphylococcus aureus* A9719] >gb|EEV70828.1|amidase [*Staphylococcus aureus* A9635] >gb|EEV73537.1|autolysin [*Staphylococcus aureus* A9299] >gb|EEV76036.1|phage amidase [*Staphylococcus aureus* A8115] >gb|EEV84456.1| | | | | |

TABLE 4-continued

Exemplary sequences producing significant alignments:

| Accession | Description | Max score | Total score | Query coverage | Value |
|---|---|---|---|---|---|
| | lytic enzyme [*Staphylococcus aureus* A5948] >emb|CBI49813.1|autolysin [*Staphylococcus aureus* subsp. *aureus* TW20] >gb|EFB43544.1|N-acetylmuramoyl-L-alanine amidase [*Staphylococcus aureus* subsp. *aureus* C101] >gb|EFB46639.1|N-acetylmuramoyl-L-alanine amidase [*Staphylococcus aureus* subsp. *aureus* C427] >gb|EFB49275.1|N-acetylmuramoyl-L-alanine amidase [*Staphylococcus aureus* subsp. *aureus* D139] >gb|EFB51786.1|gametolysin [*Staphylococcus aureus* subsp. *aureus* M899] >gb|EFB54894.1|phage amidase [*Staphylococcus aureus* subsp. *aureus* WBG10049] >gb|EFB57131.1|phage amidase [*Staphylococcus aureus* subsp. *aureus* WW2703/97] >gb|EFB60644.1|N-acetylmuramoyl-L-alanine amidase [*Staphylococcus aureus* subsp. *aureus* Btn1260] >gb|EFB97349.1|N-acetylmuramoyl-L-alanine amidase [*Staphylococcus aureus* A9765] >gb|EFB99977.1|gametolysin [*Staphylococcus aureus* subsp. *aureus* C160] >gb|EFC03126.1|N-acetylmuramoyl-L-alanine amidase [*Staphylococcus aureus* A8117] >gb|EFD96984.1|gametolysin [*Staphylococcus aureus* subsp. *aureus* M1015] >gb|EFE25153.1|N-acetylmuramoyl-L-alanine amidase [*Staphylococcus aureus* subsp. *aureus* 58-424] >gb|EFF09208.1|phage amidase [*Staphylococcus aureus* subsp. *aureus* M809] >gb|EFG40061.1|N-acetylmuramoyl-L-alanine amidase [*Staphylococcus aureus* A9754] >gb|EFG43692.1|N-acetylmuramoyl-L-alanine amidase [*Staphylococcus aureus* A8819] >gb|EFG57150.1|autolysin [*Staphylococcus aureus* subsp. *aureus* EMRSA16] >gb|EFH25468.1|N-acetylmuramoyl-L-alanine amidase [*Staphylococcus aureus* subsp. *aureus* ATCC 51811] >gb|EFH36061.1|N-acetylmuramoyl-L-alanine amidase [*Staphylococcus aureus* A8796] >gb|EFH95840.1|N-acetylmuramoyl-L-alanine amidase [*Staphylococcus aureus* subsp. *aureus* MN8] | | | | |
| ZP_06376153.1 | gametolysin [*Staphylococcus aureus* subsp. *aureus* A017934/97] >gb|EFC28569.1|gametolysin [*Staphylococcus aureus* subsp. *aureus* A017934/97] | 142 | 142 | 53% | 3e-34 |
| YP_416272.1 | lytic enzyme [*Staphylococcus aureus* RF122] >pir||JC5470 hypothetical 29.1K protein - *Staphylococcus aureus* >dbj|BAE45257.1|amidase [*Staphylococcus aureus*] >emb|CAI80469.1|lytic enzyme [*Staphylococcus aureus* RF122] >gb|ADI98373.1|lytic enzyme [*Staphylococcus aureus* subsp. *aureus* ED133] | 142 | 142 | 53% | 3e-34 |
| NP_372469.1 | lytic enzyme [*Staphylococcus aureus* subsp. *aureus* Mu50] >ref|YP_001442521.1|lytic enzyme [*Staphylococcus aureus* subsp. *aureus* Mu3] >ref|ZP_05145333.2|lytic enzyme [*Staphylococcus aureus* subsp. *aureus* Mu50-omega] >dbj|BAB58107.1|lytic enzyme [*Staphylococcus aureus* subsp. *aureus* Mu50] >dbj|BAF78814.1|lytic enzyme [*Staphylococcus aureus* subsp. *aureus* Mu3] | 142 | 142 | 53% | 4e-34 |
| YP_043983.1 | autolysin [*Staphylococcus aureus* subsp. *aureus* MSSA476] >emb|CAG43675.1|autolysin [*Staphylococcus aureus* subsp. *aureus* MSSA476] | 140 | 140 | 53% | 1e-33 |
| ZP_06343995.1 | N-acetylmuramoyl-L-alanine amidase [*Staphylococcus aureus* subsp. *aureus* H19] >gb|EFC06789.1|N-acetylmuramoyl-L-alanine amidase [*Staphylococcus aureus* subsp. *aureus* H19] | 140 | 140 | 53% | 2e-33 |
| NP_375054.1 | lytic enzyme [*Staphylococcus aureus* subsp. *aureus* N315] >ref|ZP_04840327.1|lytic enzyme [*Staphylococcus aureus* subsp. *aureus* str. CF-Marseille] >ref|ZP_05681894.1|lytic enzyme [*Staphylococcus aureus* A9763] >ref|ZP_05696065.1|autolysin [*Staphylococcus aureus* A6224] >ref|ZP_05702491.1|lytic enzyme [*Staphylococcus aureus* A5937] >ref|ZP_06335731.1|N-acetylmuramoyl-L-alanine amidase [*Staphylococcus aureus* A10102] >dbj|BAB43033.1|lytic enzyme [*Staphylococcus aureus* subsp. *aureus* N315] >gb|EEV64043.1|lytic enzyme [*Staphylococcus aureus* A9763] >gb|EEV81732.1|autolysin [*Staphylococcus aureus* A6224] >gb|EEV86142.1|lytic enzyme [*Staphylococcus aureus* A5937] >gb|EFB95269.1|N-acetylmuramoyl-L-alanine amidase [*Staphylococcus aureus* A10102] >gb|ADC38117.1|Autolysin [*Staphylococcus aureus* 04-02981] | 140 | 140 | 53% | 2e-33 |
| ZP_04867680.1 | C51 family D-Ala-D-Gly carboxypeptidase [*Staphylococcus aureus* subsp. *aureus* TCH130] >gb|EES97298.1|C51 family | 93.6 | 93.6 | 28% | 2e-19 |

TABLE 4-continued

Exemplary sequences producing significant alignments:

| Accession | Description | Max score | Total score | Query coverage | Value |
|---|---|---|---|---|---|
| | D-Ala-D-Gly carboxypeptidase [*Staphylococcus aureus* subsp. *aureus* TCH130] | | | | |
| ZP_05688913.1 | LytN protein [*Staphylococcus aureus* A9299] >gb|EEV73182.1|LytN protein [*Staphylococcus aureus* A9299] | 93.2 | 93.2 | 28% | 2e−19 |
| Q6G9W6.2 | RecName: Full = Probable cell wall hydrolase lytN; Flags: Precursor >sp|Q7A123.2|LYTN_STAAW RecName: Full = Probable cell wall hydrolase lytN; Flags: Precursor | 93.2 | 93.2 | 28% | 3e−19 |
| ZP_05644676.1 | cell wall hydrolase lytN [*Staphylococcus aureus* A9781] >ref|ZP_05682191.1|cell wall hydrolase lytN [*Staphylococcus aureus* A9763] >ref|ZP_05684607.1|cell wall hydrolase lytN [*Staphylococcus aureus* A9719] >ref|ZP_05702767.1|LytN protein [*Staphylococcus aureus* A5937] >ref|ZP_06300970.1|cell wall hydrolase lytN [*Staphylococcus aureus* A8117] >ref|ZP_06335205.1|cell wall hydrolase lytN [*Staphylococcus aureus* A10102] >ref|ZP_06815989.1|cell wall hydrolase lytN [*Staphylococcus aureus* A8819] >ref|ZP_06928293.1|cell wall hydrolase lytN [*Staphylococcus aureus* A8796] >sp|Q99UM3.2|LYTN_STAAM RecName: Full = Probable cell wall hydrolase lytN; Flags: Precursor >sp|Q7A5Y8.2|LYTN_STAAN RecName: Full = Probable cell wall hydrolase lytN; Flags: Precursor >gb|AAD23962.1|AF106851_1 LytN [*Staphylococcus aureus*] >gb|EEV28009.1|cell wall hydrolase lytN [*Staphylococcus aureus* A9781] >gb|EEV63731.1|cell wall hydrolase lytN [*Staphylococcus aureus* A9763] >gb|EEV66794.1|cell wall hydrolase lytN [*Staphylococcus aureus* A9719] >gb|EEV85950.1|LytN protein [*Staphylococcus aureus* A5937] >gb|EFB95669.1|cell wall hydrolase lytN [*Staphylococcus aureus* A10102] >gb|EFC04857.1|cell wall hydrolase lytN [*Staphylococcus aureus* A8117] >gb|EFG44792.1|cell wall hydrolase lytN [*Staphylococcus aureus* A8819] >gb|EFH37686.1|cell wall hydrolase lytN [*Staphylococcus aureus* A8796] | 93.2 | 93.2 | 28% | 3e−19 |
| NP_371771.1 | LytN protein [*Staphylococcus aureus* subsp. *aureus* Mu50] >ref|NP_374363.1|LytN protein [*Staphylococcus aureus* subsp. *aureus* N315] >ref|NP_645947.1|LytN protein [*Staphylococcus aureus* subsp. *aureus* MW2] >ref|YP_043307.1|putative cell wall hydrolase [*Staphylococcus aureus* subsp. *aureus* MSSA476] >ref|YP_001246681.1|CHAP domain-containing protein [*Staphylococcus aureus* subsp. *aureus* JH9] >ref|YP_001316471.1|CHAP domain-containing protein [*Staphylococcus aureus* subsp. *aureus* JH1] >ref|YP_001441827.1|LytN protein [*Staphylococcus aureus* subsp. *aureus* Mu3] >ref|ZP_05144635.2|LytN protein [*Staphylococcus aureus* subsp. *aureus* Mu50-omega] >ref|YP_003282132.1|cell wall hydrolase [*Staphylococcus aureus* subsp. *aureus* ED98] >ref|ZP_06857311.1|cell wall hydrolase [*Staphylococcus aureus* subsp. *aureus* MR1] >ref|ZP_06924538.1|cell wall hydrolase [*Staphylococcus aureus* subsp. *aureus* ATCC 51811] >dbj|BAB42342.1|LytN protein [*Staphylococcus aureus* subsp. *aureus* N315] >dbj|BAB57409.1|LytN protein [*Staphylococcus aureus* subsp. *aureus* Mu50] >dbj|BAB94995.1|LytN protein [*Staphylococcus aureus* subsp. *aureus* MW2] >emb|CAG42958.1|putative cell wall hydrolase [*Staphylococcus aureus* subsp. *aureus* MSSA476] >gb|ABQ49105.1|CHAP domain containing protein [*Staphylococcus aureus* subsp. *aureus* JH9] >gb|ABR52184.1| CHAP domain containing protein [*Staphylococcus aureus* subsp. *aureus* JH1] >dbj|BAF78120.1|LytN protein [*Staphylococcus aureus* subsp. *aureus* Mu3] >gb|ACY11126.1|cell wall hydrolase [*Staphylococcus aureus* subsp. *aureus* ED98] >gb|ADC37416.1|Putative cell wall hydrolase [Staphylococcus aureus 04-02981] >gb|EFH26252.1|cell wall hydrolase [*Staphylococcus aureus* subsp. *aureus* ATCC 51811] | 93.2 | 93.2 | 28% | 3e−19 |
| Q6GHI8.2 | RecName: Full = Probable cell wall hydrolase lytN; Flags: Precursor | 93.2 | 93.2 | 28% | 3e−19 |
| YP_040634.1 | putative cell wall hydrolase [*Staphylococcus aureus* subsp. *aureus* MRSA252] >ref|ZP_06313420.1|cell wall hydrolase lytN [*Staphylococcus aureus* subsp. *aureus* Btn1260] >ref|ZP_06316370.1|LytN protein [*Staphylococcus aureus* | 93.2 | 93.2 | 28% | 3e−19 |

TABLE 4-continued

Exemplary sequences producing significant alignments:

| Accession | Description | Max score | Total score | Query coverage | Value |
|---|---|---|---|---|---|
| | subsp. *aureus* WW2703/97] >ref|ZP_06326681.1|cell wall hydrolase lytN [*Staphylococcus aureus* subsp. *aureus* C427] >ref|ZP_06375441.1|cell wall hydrolase [*Staphylococcus aureus* subsp. *aureus* A017934/97] >ref|ZP_06949946.1|cell wall hydrolase [*Staphylococcus aureus* subsp. *aureus* MN8] >emb|CAG40225.1|putative cell wall hydrolase [*Staphylococcus aureus* subsp. *aureus* MRSA252] >gb|EFB47130.1|cell wall hydrolase lytN [*Staphylococcus aureus* subsp. *aureus* C427] >gb|EFB57885.1|LytN protein [*Staphylococcus aureus* subsp. *aureus* WW2703/97] >gb|EFB60371.1|cell wall hydrolase lytN [*Staphylococcus aureus* subsp. *aureus* Btn1260] >gb|EFC28956.1|cell wall hydrolase [*Staphylococcus aureus* subsp. *aureus* A017934/97] >gb|EFH94910.1|cell wall hydrolase [*Staphylococcus aureus* subsp. *aureus* MN8] | | | | |
| YP_499755.1 | cell wall hydrolase, putative [*Staphylococcus aureus* subsp. *aureus* NCTC 8325] >ref|ZP_03562970.1|cell wall hydrolase, putative [*Staphylococcus aureus* subsp. *aureus* str. JKD6008] >ref|ZP_03566530.1|cell wall hydrolase, putative [*Staphylococcus aureus* subsp. *aureus* str. JKD6009] >ref|ZP_06023533.1|LytN protein [*Staphylococcus aureus* 930918-3] >ref|ZP_06378638.1|cell wall hydrolase, putative [*Staphylococcus aureus* subsp. *aureus* 132] >gb|ABD30323.1| cell wall hydrolase, putative [*Staphylococcus aureus* subsp. *aureus* NCTC 8325] >gb|EEW45706.1|LytN protein [*Staphylococcus aureus* 930918-3] | 93.2 | 93.2 | 28% | 3e−19 |
| YP_186122.1 | cell wall hydrolase [*Staphylococcus aureus* subsp. *aureus* COL] >ref|YP_001332191.1|cell-wall hydrolase lytN [*Staphylococcus aureus* subsp. *aureus* str. Newman] >sp|Q5HGI5.1|LYTN_STAAC RecName: Full = Probable cell wall hydrolase lytN; Flags: Precursor >gb|AAW38096.1|cell wall hydrolase [*Staphylococcus aureus* subsp. *aureus* COL] >dbj|BAF67429.1|cell-wall hydrolase lytN [*Staphylococcus aureus* subsp. *aureus* str. Newman] | 93.2 | 93.2 | 28% | 3e−19 |
| ZP_06311690.1 | cell wall hydrolase [*Staphylococcus aureus* subsp. *aureus* C160] >gb|EFC00384.1|cell wall hydrolase [*Staphylococcus aureus* subsp. *aureus* C160] | 93.2 | 93.2 | 28% | 3e−19 |
| YP_493837.1 | cell wall hydrolase [*Staphylococcus aureus* subsp. *aureus* USA300_FPR3757] >ref|YP_001575072.1|C51 family D-Ala-D-Gly carboxypeptidase [*Staphylococcus aureus* subsp. *aureus* USA300_TCH1516] >ref|ZP_05700552.1|cell wall hydrolase LytN [*Staphylococcus aureus* A5948] >ref|ZP_06327760.1|cell wall hydrolase lytN [*Staphylococcus aureus* A9765] >ref|ZP_06788989.1|cell wall hydrolase lytN [*Staphylococcus aureus* A9754] >sp|Q9ZNI1.2|LYTN_STAA8 RecName: Full = Probable cell wall hydrolase lytN; Flags: Precursor >gb|ABD22392.1|cell wall hydrolase [*Staphylococcus aureus* subsp. *aureus* USA300_FPR3757] >gb|ABX29193.1|C51 family D-Ala-D-Gly carboxypeptidase [*Staphylococcus aureus* subsp. *aureus* USA300_TCH1516] >gb|EEV82606.1|cell wall hydrolase LytN [*Staphylococcus aureus* A5948] >gb|EFB99731.1|cell wall hydrolase lytN [*Staphylococcus aureus* A9765] >gb|EFG41464.1|cell wall hydrolase lytN [*Staphylococcus aureus* A9754] | 93.2 | 93.2 | 28% | 3e−19 |
| ZP_04866031.1 | C51 family D-Ala-D-Gly carboxypeptidase [*Staphylococcus aureus* subsp. *aureus* USA300_TCH959] >gb|EES93005.1| C51 family D-Ala-D-Gly carboxypeptidase [*Staphylococcus aureus* subsp. *aureus* USA300_TCH959] | 93.2 | 93.2 | 28% | 3e−19 |
| ZP_05692914.1 | LytN protein [*Staphylococcus aureus* A8115] >ref|ZP_05695726.1|LytN, cell wall hydrolase [*Staphylococcus aureus* A6300] >ref|ZP_05697527.1|LytN, cell wall hydrolase [*Staphylococcus aureus* A6224] >gb|EEV74031.1|LytN protein [*Staphylococcus aureus* A8115] >gb|EEV76732.1|LytN, cell wall hydrolase [*Staphylococcus aureus* A6300] >gb|EEV80310.1|LytN, cell wall hydrolase [*Staphylococcus aureus* A6224] | 93.2 | 93.2 | 28% | 3e−19 |
| ZP_04018132.1 | C51 family D-Ala-D-Gly carboxypeptidase [*Staphylococcus aureus* subsp. *aureus* TCH60] >ref|ZP_06318622.1|LytN protein [*Staphylococcus aureus* subsp. *aureus* WBG10049] >gb|EEJ61188.1|C51 family D-Ala-D-Gly carboxypeptidase [*Staphylococcus aureus* subsp. *aureus* TCH60] >gb|EFB55733.1|LytN protein [*Staphylococcus aureus* subsp. *aureus* WBG10049] | 93.2 | 93.2 | 28% | 3e−19 |

TABLE 4-continued

Exemplary sequences producing significant alignments:

| Accession | Description | Max score | Total score | Query coverage | Value |
|---|---|---|---|---|---|
| BAA33856.1 | LytN [*Staphylococcus aureus*] | 92.8 | 92.8 | 28% | 3e−19 |
| ZP_05686797.1 | conserved hypothetical protein [*Staphylococcus aureus* A9635] >gb|EEV69970.1|conserved hypothetical protein [*Staphylococcus aureus* A9635] | 92.8 | 92.8 | 28% | 3e−19 |
| ZP_06820366.1 | cell wall hydrolase lytN [*Staphylococcus aureus* subsp. *aureus* EMRSA16] >gb|EFG57726.1|cell wall hydrolase lytN [*Staphylococcus aureus* subsp. *aureus* EMRSA16] | 92.8 | 92.8 | 28% | 3e−19 |
| ZP_05606977.1 | cell-wall hydrolase lytN [*Staphylococcus aureus* subsp. *aureus* 68-397] >ref|ZP_06666907.1|cell-wall hydrolase lytN [*Staphylococcus aureus* subsp. *aureus* 58-424] >ref|ZP_06668726.1|cell-wall hydrolase lytN [*Staphylococcus aureus* subsp. *aureus* M809] >gb|EEV09342.1|cell-wall hydrolase lytN [*Staphylococcus aureus* subsp. *aureus* 68-397] >gb|EFE26322.1|cell-wall hydrolase lytN [*Staphylococcus aureus* subsp. *aureus* 58-424] >gb|EFF09480.1|cell-wall hydrolase lytN [*Staphylococcus aureus* subsp. *aureus* M809] | 92.8 | 92.8 | 28% | 4e−19 |
| YP_001246290.1 | CHAP domain-containing protein [*Staphylococcus aureus* subsp. *aureus* JH9] >ref|YP_001316074.1|CHAP domain-containing protein [*Staphylococcus aureus* subsp. *aureus* JH1] >ref|ZP_05644375.1|CHAP domain-containing protein [*Staphylococcus aureus* A9781] >ref|ZP_05682372.1|CHAP domain-containing protein [*Staphylococcus aureus* A9763] >ref|ZP_05683330.1|CHAP domain-containing protein [*Staphylococcus aureus* A9719] >ref|ZP_05698572.1|CHAP domain-containing protein [*Staphylococcus aureus* A6224] >ref|ZP_05701834.1|CHAP domain-containing protein [*Staphylococcus aureus* A5937] >ref|ZP_06336692.1|CHAP domain-containing protein [*Staphylococcus aureus* A10102] >ref|ZP_06817465.1|CHAP domain-containing protein [*Staphylococcus aureus* A8819] >ref|ZP_06930537.1|CHAP domain-containing protein [*Staphylococcus aureus* A8796] >gb|ABQ48714.1|CHAP domain containing protein [*Staphylococcus aureus* subsp. *aureus* JH9] >gb|ABR51787.1| CHAP domain containing protein [*Staphylococcus aureus* subsp. *aureus* JH1] >gb|EEV27708.1|CHAP domain-containing protein [*Staphylococcus aureus* A9781] >gb|EEV63379.1|CHAP domain-containing protein [*Staphylococcus aureus* A9763] >gb|EEV68032.1|CHAP domain-containing protein [*Staphylococcus aureus* A9719] >gb|EEV79159.1|CHAP domain-containing protein [*Staphylococcus aureus* A6224] >gb|EEV86483.1|CHAP domain-containing protein [*Staphylococcus aureus* A5937] >gb|EFB94397.1|CHAP domain-containing protein [*Staphylococcus aureus* A10102] >gb|ADC37080.1|Lytic enzyme, amidase [Staphylococcus phage phiSaST5K] >gb|EFG43487.1|CHAP domain-containing protein [*Staphylococcus aureus* A8819] >gb|EFH35702.1|CHAP domain-containing protein [*Staphylococcus aureus* A8796] | 87.8 | 87.8 | 37% | 1e−17 |
| ZP_04865682.1 | bacteriophage amidase [*Staphylococcus aureus* subsp. *aureus* USA300_TCH959] >gb|EES93489.1|bacteriophage amidase [*Staphylococcus aureus* subsp. *aureus* USA300_TCH959] | 85.9 | 85.9 | 37% | 4e−17 |
| ZP_06378624.1 | phage amidase [*Staphylococcus aureus* subsp. *aureus* 132] | 85.9 | 85.9 | 37% | 5e−17 |
| ZP_06859762.1 | phage amidase [*Staphylococcus aureus* subsp. *aureus* MR1] | 85.9 | 85.9 | 37% | 5e−17 |
| ZP_05694219.1 | CHAP domain-containing protein [*Staphylococcus aureus* A6300] >gb|EEV78056.1|CHAP domain-containing protein [*Staphylococcus aureus* A6300] | 85.5 | 85.5 | 37% | 5e−17 |
| ZP_04840337.1 | CHAP domain-containing protein [*Staphylococcus aureus* subsp. *aureus* str. CF-Marseille] | 85.5 | 85.5 | 37% | 5e−17 |
| YP_003281797.1 | phage amidase [*Staphylococcus aureus* subsp. *aureus* ED98] >gb|ACY10791.1|phage amidase [*Staphylococcus aureus* subsp. *aureus* ED98] | 85.5 | 85.5 | 37% | 5e−17 |
| ADI97635.1 | Phage amidase [*Staphylococcus aureus* subsp. *aureus* ED133] | 83.2 | 83.2 | 40% | 2e−16 |
| ACZ59017.1 | Lytic enzyme, amidase [*Staphylococcus aureus*] | 77.4 | 77.4 | 27% | 1e−14 |
| YP_417168.1 | phage-related cell wall hydrolase [*Staphylococcus aureus* RF122] >emb|CAI81395.1|phage-related cell wall hydrolase [*Staphylococcus aureus* RF122] | 75.1 | 75.1 | 62% | 7e−14 |
| CBI50050.1 | phage amidase [*Staphylococcus aureus* subsp. *aureus* TW20] | 73.6 | 73.6 | 30% | 2e−13 |
| ZP_04865678.1 | hypothetical protein HMPREF0776_1895 [*Staphylococcus aureus* subsp. *aureus* USA300_TCH959] >gb|EES93485.1| hypothetical protein HMPREF0776_1895 [*Staphylococcus aureus* subsp. *aureus* USA300_TCH959] | 72.4 | 72.4 | 73% | 4e−13 |

TABLE 4-continued

Exemplary sequences producing significant alignments:

| Accession | Description | Max score | Total score | Query coverage | Value |
|---|---|---|---|---|---|
| ZP_06948773.1 | N-acetylmuramoyl-L-alanine amidase [*Staphylococcus aureus* subsp. *aureus* MN8] >gb\|EFH95975.1\|N-acetylmuramoyl-L-alanine amidase [*Staphylococcus aureus* subsp. *aureus* MN8] | 71.6 | 71.6 | 73% | 9e−13 |
| ZP_04837774.1 | mannosyl-glycoprotein endo-beta-N-acetylglucosaminidase [*Staphylococcus aureus* subsp. *aureus* str. CF-Marseille] | 71.2 | 71.2 | 79% | 9e−13 |
| ZP_06378620.1 | mannosyl-glycoprotein endo-beta-N-acetylglucosaminidase [*Staphylococcus aureus* subsp. *aureus* 132] | 71.2 | 71.2 | 79% | 1e−12 |
| ZP_06343859.1 | mannosyl-glycoprotein endo-beta-N-acetylglucosaminidase [*Staphylococcus aureus* subsp. *aureus* H19] >gb\|EFC06653.1\| mannosyl-glycoprotein endo-beta-N-acetylglucosaminidase [*Staphylococcus aureus* subsp. *aureus* H19] | 71.2 | 71.2 | 73% | 1e−12 |
| ZP_05687283.1 | conserved hypothetical protein [*Staphylococcus aureus* A9635] >gb\|EEV69450.1\|conserved hypothetical protein [*Staphylococcus aureus* A9635] | 70.9 | 70.9 | 79% | 1e−12 |
| ZP_05609593.1 | tail tip protein [*Staphylococcus aureus* subsp. *aureus* E1410] >gb\|EEV11465.1\|tail tip protein [*Staphylococcus aureus* subsp. *aureus* E1410] | 70.9 | 70.9 | 79% | 2e−12 |
| YP_001245745.1 | mannosyl-glycoprotein endo-beta-N-acetylglucosaminidase [*Staphylococcus aureus* subsp. *aureus* JH9] >ref\|YP_001315521.1\|mannosyl-glycoprotein endo-beta-N-acetylglucosaminidase [*Staphylococcus aureus* subsp. *aureus* JH1] >ref\|ZP_05696129.1\|mannosyl-glycoprotein endo-beta-N-acetylglucosaminidase [*Staphylococcus aureus* A6224] >gb\|ABQ48169.1\|Mannosyl-glycoprotein endo-beta-N-acetylglucosaminidase [*Staphylococcus aureus* subsp. *aureus* JH9] >gb\|ABR51234.1\|Mannosyl-glycoprotein endo-beta-N-acetylglucosaminidase [*Staphylococcus aureus* subsp. *aureus* JH1] >gb\|EEV81607.1\|mannosyl-glycoprotein endo-beta-N-acetylglucosaminidase [*Staphylococcus aureus* A6224] | 70.5 | 70.5 | 79% | 2e−12 |
| ZP_03562546.1 | mannosyl-glycoprotein endo-beta-N-acetylglucosaminidase [*Staphylococcus aureus* subsp. *aureus* str. JKD6008] >ref\|ZP_03566885.1\|mannosyl-glycoprotein endo-beta-N-acetylglucosaminidase [*Staphylococcus aureus* subsp. *aureus* str. JKD6009] | 70.5 | 70.5 | 79% | 2e−12 |
| ZP_06859693.1 | mannosyl-glycoprotein endo-beta-N-acetylglucosaminidase [*Staphylococcus aureus* subsp. *aureus* MR1] >emb\|CBI48268.1\|putative cell wall hydrolase [*Staphylococcus aureus* subsp. *aureus* TW20] | 69.7 | 69.7 | 79% | 3e−12 |
| ZP_06817534.1 | mannosyl-glycoprotein endo-beta-N-acetylglucosaminidase [*Staphylococcus aureus* A8819] >ref\|ZP_06930722.1\| mannosyl-glycoprotein endo-beta-N-acetylglucosaminidase [*Staphylococcus aureus* A8796] >gb\|EFG43426.1\|mannosyl-glycoprotein endo-beta-N-acetylglucosaminidase [*Staphylococcus aureus* A8819] >gb\|EFH35511.1\|mannosyl-glycoprotein endo-beta-N-acetylglucosaminidase [*Staphylococcus aureus* A8796] | 69.7 | 69.7 | 79% | 3e−12 |
| ADI96879.1 | prophage amidase, putative [*Staphylococcus aureus* subsp. *aureus* ED133] | 58.9 | 95.9 | 59% | 5e−09 |
| YP_040898.1 | amidase [*Staphylococcus aureus* subsp. *aureus* MRSA252] >ref\|ZP_06820630.1\|N-acetylmuramoyl-L-alanine amidase [*Staphylococcus aureus* subsp. *aureus* EMRSA16] >ref\|ZP_06949669.1\|bacteriophage amidase [*Staphylococcus aureus* subsp. *aureus* MN8] >emb\|CAG40495.1\|amidase [*Staphylococcus aureus* subsp. *aureus* MRSA252] >gb\|EFG57990.1\|N-acetylmuramoyl-L-alanine amidase [*Staphylococcus aureus* subsp. *aureus* EMRSA16] >gb\|EFH94633.1\|bacteriophage amidase [*Staphylococcus aureus* subsp. *aureus* MN8] | 58.9 | 94.7 | 59% | 5e−09 |
| YP_003282866.1 | putative amidase [*Staphylococcus aureus* subsp. *aureus* ED98] >gb\|ACY11860.1\|putative amidase [*Staphylococcus aureus* subsp. *aureus* ED98] | 57.4 | 98.6 | 60% | 2e−08 |
| CAQ48834.1 | amidase [*Staphylococcus aureus* subsp. *aureus* ST398] | 57.0 | 92.8 | 67% | 2e−08 |
| YP_185281.1 | prophage L54a, amidase, putative [*Staphylococcus aureus* subsp. *aureus* COL] >gb\|AAW38858.1\|prophage L54a, amidase, putative [*Staphylococcus aureus* subsp. *aureus* COL] | 56.6 | 92.4 | 59% | 3e−08 |
| YP_001331347.1 | amidase [*Staphylococcus aureus* subsp. *aureus* str. Newman] >ref\|YP_001332803.1\|phage amidase [*Staphylococcus aureus* subsp. *aureus* str. Newman] >dbj\|BAF66585.1\| amidase [*Staphylococcus aureus* subsp. *aureus* str. Newman] >dbj\|BAF68041.1\|phage amidase [*Staphylococcus aureus* subsp. *aureus* str. Newman] | 56.6 | 90.9 | 59% | 3e−08 |
| ZP_06859771.1 | petidoglycan hydrolase, putative [*Staphylococcus aureus* subsp. *aureus* MR1] | 54.7 | 54.7 | 32% | 1e−07 |

TABLE 4-continued

Exemplary sequences producing significant alignments:

| Accession | Description | Max score | Total score | Query coverage | Value |
|---|---|---|---|---|---|
| ZP_06930779.1 | N-acetylmuramoyl-L-alanine amidase [*Staphylococcus aureus* A8796] >gb|EFH35454.1|N-acetylmuramoyl-L-alanine amidase [*Staphylococcus aureus* A8796] | 54.7 | 54.7 | 32% | 1e−07 |
| ZP_06924283.1 | bacteriophage amidase [*Staphylococcus aureus* subsp. *aureus* ATCC 51811] >gb|EFH26464.1|bacteriophage amidase [*Staphylococcus aureus* subsp. *aureus* ATCC 51811] | 54.3 | 88.2 | 59% | 1e−07 |
| NP_646197.1 | truncated amidase [*Staphylococcus aureus* subsp. *aureus* MW2] >ref|ZP_05601979.1|amidase [*Staphylococcus aureus* subsp. *aureus* 55/2053] >ref|ZP_05607225.1|amidase [*Staphylococcus aureus* subsp. *aureus* 68-397] >ref|ZP_05612490.1|amidase [*Staphylococcus aureus* subsp. *aureus* M876] >ref|ZP_06322067.1|putative prophage L54a, amidase [*Staphylococcus aureus* subsp. *aureus* M899] >ref|ZP_06332149.1|N-acetylmuramoyl-L-alanine amidase [*Staphylococcus aureus* subsp. *aureus* C101] >ref|ZP_06667156.1|N-acetylmuramoyl-L-alanine amidase [*Staphylococcus aureus* subsp. *aureus* 58-424] >ref|ZP_06668976.1|N-acetylmuramoyl-L-alanine amidase [*Staphylococcus aureus* subsp. *aureus* M809] >ref|ZP_06671546.1|putative prophage L54a, amidase [*Staphylococcus aureus* subsp. *aureus* M1015] >dbj|BAB95245.1|truncated amidase [*Staphylococcus aureus* subsp. *aureus* MW2] >gb|EEV04149.1|amidase [*Staphylococcus aureus* subsp. *aureus* 55/2053] >gb|EEV09590.1|amidase [*Staphylococcus aureus* subsp. *aureus* 68-397] >gb|EEV14845.1|amidase [*Staphylococcus aureus* subsp. *aureus* M876] >gb|EFB43966.1|N-acetylmuramoyl-L-alanine amidase [*Staphylococcus aureus* subsp. *aureus* C101] >gb|EFB52672.1|putative prophage L54a, amidase [*Staphylococcus aureus* subsp. *aureus* M899] >gb|EFD97409.1|putative prophage L54a, amidase [*Staphylococcus aureus* subsp. *aureus* M1015] >gb|EFE26571.1|N-acetylmuramoyl-L-alanine amidase [*Staphylococcus aureus* subsp. *aureus* 58-424] >gb|EFF09418.1|N-acetylmuramoyl-L-alanine amidase [*Staphylococcus aureus* subsp. *aureus* M809] | 54.3 | 86.6 | 59% | 1e−07 |
| ZP_06334988.1 | N-acetylmuramoyl-L-alanine amidase [*Staphylococcus aureus* A10102] >gb|EFB95770.1|N-acetylmuramoyl-L-alanine amidase [*Staphylococcus aureus* A10102] | 54.3 | 89.7 | 59% | 1e−07 |
| ZP_04017867.1 | bacteriophage amidase [*Staphylococcus aureus* subsp. *aureus* TCH60] >ref|ZP_06318869.1|amidase [*Staphylococcus aureus* subsp. *aureus* WBG10049] >gb|EEJ61820.1|bacteriophage amidase [*Staphylococcus aureus* subsp. *aureus* TCH60] >gb|EFB55072.1|amidase [*Staphylococcus aureus* subsp. *aureus* WBG10049] | 54.3 | 89.0 | 59% | 1e−07 |
| ZP_05696927.1 | amidase [*Staphylococcus aureus* A6224] >ref|ZP_05703499.1|amidase [*Staphylococcus aureus* A5937] >gb|EEV80745.1|amidase [*Staphylococcus aureus* A6224] >gb|EEV85001.1|amidase [*Staphylococcus aureus* A5937] | 54.3 | 89.0 | 59% | 1e−07 |
| ZP_05693770.1 | amidase [*Staphylococcus aureus* A6300] >gb|EEV78568.1|amidase [*Staphylococcus aureus* A6300] | 54.3 | 88.2 | 59% | 1e−07 |
| ZP_06378887.1 | petidoglycan hydrolase, putative [*Staphylococcus aureus* subsp. *aureus* 132] | 54.3 | 88.2 | 59% | 1e−07 |
| YP_494080.1 | phiSLT ORF484-like protein, lysin [*Staphylococcus aureus* subsp. *aureus* USA300_FPR3757] >ref|YP_001575320.1|bacteriophage amidase [*Staphylococcus aureus* subsp. *aureus* USA300_TCH1516] >gb|ABD20547.1|phiSLT ORF484-like protein, lysin [*Staphylococcus aureus* subsp. *aureus* USA300_FPR3757] >gb|ABX29441.1|bacteriophage amidase [*Staphylococcus aureus* subsp. *aureus* USA300_TCH1516] | 53.9 | 89.7 | 58% | 2e−07 |
| YP_500032.1 | petidoglycan hydrolase, putative [*Staphylococcus aureus* subsp. *aureus* NCTC 8325] >gb|ABD30597.1|petidoglycan hydrolase, putative [*Staphylococcus aureus* subsp. *aureus* NCTC 8325] | 53.9 | 87.8 | 59% | 2e−07 |
| ZP_06817547.1 | N-acetylmuramoyl-L-alanine amidase [*Staphylococcus aureus* A8819] >gb|EFG43415.1|N-acetylmuramoyl-L-alanine amidase [*Staphylococcus aureus* A8819] | 53.9 | 53.9 | 41% | 2e−07 |
| ZP_06930778.1 | N-acetylmuramoyl-L-alanine amidase [*Staphylococcus aureus* A8796] >gb|EFH35455.1|N-acetylmuramoyl-L-alanine amidase [*Staphylococcus aureus* A8796] | 53.9 | 53.9 | 32% | 2e−07 |
| ZP_05604610.1 | amidase [*Staphylococcus aureus* subsp. *aureus* 65-1322] >gb|EEV06540.1|amidase [*Staphylococcus aureus* subsp. *aureus* 65-1322] | 53.5 | 83.6 | 52% | 2e−07 |

TABLE 4-continued

Exemplary sequences producing significant alignments:

| Accession | Description | Max score | Total score | Query coverage | Value |
|---|---|---|---|---|---|
| ZP_06329456.1 | N-acetylmuramoyl-L-alanine amidase [*Staphylococcus aureus* A9765] >gb|EFB98990.1|N-acetylmuramoyl-L-alanine amidase [*Staphylococcus aureus* A9765] | 53.1 | 87.0 | 59% | 3e−07 |
| ZP_05683225.1 | amidase [*Staphylococcus aureus* A9719] >gb|EEV68105.1| amidase [*Staphylococcus aureus* A9719] | 53.1 | 87.8 | 59% | 3e−07 |
| ZP_05693263.1 | predicted protein [*Staphylococcus aureus* A6300] >gb|EEV79042.1|predicted protein [*Staphylococcus aureus* A6300] | 52.8 | 52.8 | 24% | 4e−07 |
| YP_043081.1 | amidase [*Staphylococcus aureus* subsp. *aureus* MSSA476] >emb|CAG42730.1|amidase [*Staphylococcus aureus* subsp. *aureus* MSSA476] | 52.4 | 86.6 | 59% | 5e−07 |
| ZP_05610313.1 | conserved hypothetical protein [*Staphylococcus aureus* subsp. *aureus* E1410] >gb|EEV11278.1|conserved hypothetical protein [*Staphylococcus aureus* subsp. *aureus* E1410] | 47.0 | 47.0 | 19% | 2e−05 |
| ZP_05610314.1 | amidase [*Staphylococcus aureus* subsp. *aureus* E1410] >gb|EEV11277.1|amidase [*Staphylococcus aureus* subsp. *aureus* E1410] | 45.4 | 45.4 | 19% | 6e−05 |
| ZP_06324259.1 | predicted protein [*Staphylococcus aureus* subsp. *aureus* D139] >ref|ZP_06343202.1|predicted protein [*Staphylococcus aureus* subsp. *aureus* H19] >gb|EFB50285.1| predicted protein [*Staphylococcus aureus* subsp. *aureus* D139] >gb|EFC07547.1|predicted protein [*Staphylococcus aureus* subsp. *aureus* H19] | 37.0 | 37.0 | 10% | 0.020 |
| CAQ49671.1 | LytN protein [*Staphylococcus aureus* subsp. *aureus* ST398] | 37.0 | 37.0 | 10% | 0.022 |
| ZP_06930329.1 | predicted protein [*Staphylococcus aureus* A8796] >gb|EFH35860.1|predicted protein [*Staphylococcus aureus* A8796] | 36.2 | 36.2 | 8% | 0.043 |
| ZP_05688584.1 | amidase [*Staphylococcus aureus* A9299] >gb|EEV73312.1| amidase [*Staphylococcus aureus* A9299] | 35.8 | 70.5 | 42% | 0.049 |

The first 21 sequences of Table 4 have very high similarity as will be understood by a skilled person. According to an experimental approach directed to minimize the number of sequences to be analyzed 2-3 sequences can be chosen from this set and then subjected to a further screen level. Then 2 or 3 sequences or so can be selected from the next set, which happens to have a similarity of ~53%. After the second round of such a selection the expectation that the proteins below the threshold would behave similarly to the Twort endolysin is low. Any sequence that is from phage is immediately eliminated. Of the remaining sequences, the genomic region around the chosen gene are checked to ensure that it is not part of or a remnant of a prophage.

The proteins encoded by these genes are expressed and tested according to the procedures for antimicrobial activity according to methods herein described.

The examples set forth above are provided to give those of ordinary skill in the art a complete disclosure and description of how to make and use the embodiments of the targeted antimicrobials, and related compositions, methods and systems herein described, and are not intended to limit the scope of what the inventors regard as their disclosure. Modifications of the above-described modes for carrying out the disclosure that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

The entire disclosure of each document cited (including patents, patent applications, journal articles, abstracts, laboratory manuals, books, or other disclosures) in the Background, Summary, Detailed Description, and Examples is hereby incorporated herein by reference. Further, the sequence listing submitted herewith with the file name P622-USC-2016-08-01.txt created on Aug. 1, 2016 is incorporated herein by reference in its entirety.

It is to be understood that the disclosures are not limited to particular compositions or biological systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

Although any methods and materials similar or equivalent to those described herein can be used in the practice for testing of the products, methods and system of the present disclosure, exemplary appropriate materials and methods are described herein for guidance purposes.

A number of embodiments of the disclosure have been described. Nevertheless, it will be understood that various modifications may be made without departing from the spirit and scope of the present disclosure. Accordingly, other embodiments are within the scope of the following claims.

REFERENCES

1. Beernink, P. T., B. W. Segelke, and M. A. Coleman. 2003. High-Throughput, Cell-Free Protein Expression Screening Using the RTS 100 *E. coli* HY Kit. Biochemica 1:4-5.
2. Borysowski, J., B. Weber-Dabrowska, and A. Górski. 2006. Bacteriophage Endolysins as a Novel Class of Antibacterial Agents. Exp. Biol. Med. 231:366-377.

3. Challacomb, J. F., M. R. Altherr, G. Xie, S. S. Bhotika, N. Brown, D. Bruce, C. S. Campbell, M. L. Campbell, J. Chen, O. Chertkov, C. Cleland, M. Dimitrijevic, N. A. Doggett, J. J. Fawcett, T. Glavina, L. A. Goodwin, L. D. Green, C. S. Han, K. K. Hill, P. Hitchcock, P. J. Jackson, P. Keim, A. R. Kewalramani, J. Longmire, S. Lucas, S. Malfatti, D. Martinez, K. McMurry, L. J. Meincke, M. Misra, B. L. Moseman, M. Mundt, A. C. Munk, R. T. Okinaka, B. Parson-Quintana, L. P. Reilly, P. Richardson, D. L. Robinson, E. Saunders, R. Tapia, J. G. Tesmer, N. Thayer, L. S. Thompson, H. Tice, L. O. Ticknor, P. L. Wills, P. Gilna, and T. S. Brettin. 2007. The Complete Genome Sequence of *Bacillus thuringiensis* Al Hakam. J. Bacteriol. 189:3680-3681.

4. Fischetti, V. A. 2004. The use of phage lytic enzymes to control bacterial infections. p. 321-334. In: E. Kutter, A. Sulakvelidze, (ed.), Bacteriophages: Biology and Applications. CRC Press, Boca Raton.

5. Guenther, S., D. Huwyler, S. Richard, and M. J. Leossner. 2009. Virulent bacteriophage for efficient biocontrol of *Listeria monocytogenes* in Ready-To-Eat Foods. Appl. Environ. Microbiol. 75:93-100.

6. Han, C. S., G. Xie, J. F. Challacombe, M. R. Altherr, S. S. Bhotika, D. Bruce, C. S. Campbell, M. L. Campbell, J. Chen, O. Chertkov, C. Cleland, M. Dimitrijevic, N. A. Doggett, J. J. Fawcett, T. Glavina, L. A. Goodwin, K. K. Hill, P. Hitchcock, P. J. Jackson, P. Keim, A. R. Kewalramani, J. Longmire, S. Lucas, S. Malfatti, K. McMurry, L. J. Meincke, M. Misra, B. L. Moseman, M. Mundt, A. C. Munk. R. T. Okinaka, B. Parson-Quintana, L. P. Reilly, P. Richardson, D. L. Robinson, E. Rubin, E. Saunders, R. Tapia, J. G. Tesmer, N. Thayer, L. S. Thompson, H. Tice, L. O. Ticknor, P. L. Wills, T. S. Brettin and P. Gilna. 2006. Pathogenic sequence analysis of *Bacillus cereus* and *Bacillus thuringiensis* isolates closely related to *Bacillus anthracis*. J. Bacteriol. 188:3382-3390.

7. Hernandez, E., F. Ramisse, J. P. Ducoureau, T. Cruel, and J. D. Cavallo. 1998. *Bacillus thuringiensis* subsp. *konkukian* (serotype H34) superinfection: case report and experimental evidence of pathogenicity in immunosuppressed mice. J. Clin. Microbiol. 36:2138-2139.

8. Hill, K. K., L. O. Ticknor, R. T. Okinaka, M. Asay, H. Blair, K. A. Bliss, M. Laker, P. E. Pardington, A. P. Richardson, M. Tonks, D. J. Beecher, J. D. Kemp, A.-B. Kolstø, A. C. L. Wong, P. Keim and P. J. Jackson. 2004. Fluorescent Amplified Fragment Length Polymorphism Analysis of *Bacillus anthracis, Bacillus cereus*, and *Bacillus thuringiensis* Isolates. Appl. Environ. Microbiol. 70:1068-1080.

9. Hoffmaster, A. R., K. K. Hill, J. E. Gee, C. K. Marston, B. K. De, T. Popovic, D. Sue, P. P. Wilkins, S. B. Avashia, R. Drumgoole, C. H. Helma, L. O. Ticknor, R. T. Okinaka, and P. J. Jackson. 2006. Characterization of *Bacillus cereus* isolates associated with fatal pneumonias: Strains are closely related to *Bacillus anthracis* and harbor *B. anthracis* virulence genes. J. Clin. Microbiol. 44:3342-3360.

10. Jacobs, C., L. J. Huang, E. Bartowsky, S. Normark, and J. T. Park. 1994. Bacterial cell wall recycling provides cytosolic muropeptides as effectors for beta-lactamase induction. EMBO J. 13:4684-4694.

11. Jacobs, C., B. Joris, M. Jami, K. Klarsov, J. Van Beeumen, D. Mengin-Lecreulx, J. van Heijenoort, J. T. Park, S, Normark, and J. M. Frere. 1995. AmpD, essential for both beta-lactamase regulation and cell wall recycling, is a novel cytosolic N-acetylmuramyl-L-alanine amidase. Mol. Microbiol. 15:553-559.

12. Jensen, O. N., W. Matthias, A. Shevckenko, and M. Mann. 1998. Peptide sequencing of 2-DE Gel-Isolated Proteins by Nanoelectrospray Tandem Mass Spectrometry. Methods Mol. Biol. 112:571-588.

13. Kwon, D. H. and L. Chung-Dar. 2006. Polyamines increase antibiotic susceptibility in *Pseudomonas aeruginosa*. Antimicrob. Agents Chemother. 50:1623-1627.

14. Loessner, M. J. 2005. Bacteriophage endolysins-current state of research and applications. Curr. Opin. Microbiol. 8:480-487, 2005

15. Loessner, M. J., K. Kramer, F. Ebel, and S. Scherer. 2002. C-terminal domains of *Listeria monocytogenes* bacteriophage murein hydrolases determine specific recognition and high-affinity binding to bacterial cell wall carbohydrates. Mol. Microbiol. 44:335-339.

16. Loessner, M. J., A. Schneider, and S. Scherer. 1996. Modified *Listeria* bacteriophage lysin genes (ply) allow efficient overexpression and one-step purification of biochemically active fusion proteins. Appl. Environ. Microbiol. 62:3057-3060.

17. Lopez, R., E. Garcí a, and J. L. Garcí a. 1997. The Pneumococcal Cell Wall Degrading Enzymes: A Modular Design to Create New Lysins? Microb. Drug Resist. 3:199-211.

18. Low, L. Y., C. Yang, M. Perego, A. Osterman, and R. C. Liddington. 2005. Structure and Lytic Activity of a *Bacillus anthracis* Prophage Endolysin. J. Biol. Chem. 280: 35433-35439.

19. Obesoa, J. M., B. Martineza, A. Rodrigueza, and P. Garcí a. 2008. Lytic activity of the recombinant staphylococcal bacteriophage ΦH5 endolysin active against *Staphylococcus aureus* in milk. Int. J. Food Microbiol. 128:212-218.

20. Rollins, S. M., A. Peppercorn, J. S. Young, M. Drysdale, A. Baresch, M. V. Bikowski, D. A. Ashford, C. P. Quinn, M. Handfield, J. D. Hillman, C. R. Lyons, T. M. Koehler, S. B. Calderwood, and E. T. Ryan. 2008. Application of in vivo induced antigen technology (IVIAT) to *Bacillus anthracis*. PLoS ONE 3:e1824.

21. Ruhfel, R. E., and C. B. Thorne. 1988. Physical and genetic characterization of the *Bacillus thuringiensis* subsp. *kurstaki* HD-1 extrachromosomal temperate phage TP-21. Abst. Ann. Meet. American Society for Microbiology, p. 145.

22. Saile, E., and T. M. Koehler. 2006. *Bacillus anthracis* multiplication, persistence, and genetic exchange in the rhizosphere of grass plants. Appl. Environ. Microbiol. 72:3168-3174.

What is claimed is:

1. An antimicrobial composition comprising an effective amount of a targeted antimicrobial protein for *Bacillus cereus* or a microorganism related thereto,
a suitable vehicle, and
one or more polyamines and/or polymixins,
wherein the targeted antimicrobial protein has a catalytic domain and a binding domain, the targeted antimicrobial protein being BCZK2532 protein having SEQ ID NO: 3 and/or a related lysin protein having lytic activity,
wherein the related lysin protein has at least a 40% percentage identity with the BCZK2532 protein having SEQ ID NO: 3 or a portion thereof, and
wherein the related lysin protein has an arginine in a position corresponding upon alignment to amino acid residue 100 of SEQ ID NO: 3.

2. The antimicrobial composition of claim 1, wherein the microorganism related thereto comprises *B. anthracis, B. thuringiensis* 97-27, *B. thuringiensis* HD1, *B. thuringiensis* HD560 and *B. thuringiensis* HD658.

3. The antimicrobial composition of claim 1, wherein the related lysin protein has at least a 50% identity with the BCZK2532 protein or a portion thereof.

4. The antimicrobial composition of claim 1, wherein the related lysin protein has at least an identity between 60% and 90% with the BCZK2532 protein or a portion thereof.

5. The antimicrobial composition of claim 1, wherein the related lysin protein has at least a 90% identity with the BCZK2532 protein or a portion thereof.

6. The antimicrobial composition of claim 1, wherein the related lysin protein has at least a 95% identity with the BCZK2532 protein or a portion thereof.

7. The antimicrobial composition of claim 1, wherein the portion thereof is the catalytic domain and/or the binding domain of the BCZK2532 protein and wherein the catalytic domain and/or the binding domain of the related lysin protein has at least a 40% identity with the catalytic domain and/or the binding domain of the BCZK2532 protein.

8. The antimicrobial composition of claim 1, wherein the portion thereof is the catalytic domain and/or the binding domain of the BCZK2532 protein and wherein the catalytic domain and/or the binding domain of the related lysin protein has at least a 50% identity with the catalytic domain and/or the binding domain of the BCZK2532 protein.

9. The antimicrobial composition of claim 1, wherein the portion thereof is the catalytic domain and/or the binding domain of the BCZK2532 protein and wherein the catalytic domain and/or the binding domain of the related lysin protein has an identity of between 60% and 90% with the catalytic domain and/or the binding domain of the BCZK2532 protein.

10. The antimicrobial composition of claim 1, wherein the portion thereof is the catalytic domain and/or the binding domain of the BCZK2532 protein and wherein the catalytic domain and/or the binding domain of the related lysin protein has at least a 90% identity with the catalytic domain and/or the binding domain of the BCZK2532 protein.

11. The antimicrobial composition of claim 1, wherein the portion thereof is the catalytic domain and/or the binding domain of the BCZK2532 protein and wherein the catalytic domain and/or the binding domain of the related lysin protein has at least a 95% identity with the catalytic domain and/or the binding domain of the BCZK2532 protein.

12. The antimicrobial composition of claim 1, wherein the composition comprises an additional one or more antimicrobials.

13. The antimicrobial composition of claim 12, wherein the antimicrobial is one or more antibiotics.

14. The antimicrobial composition of claim 1, wherein the vehicle is a pharmaceutically acceptable vehicle and the composition is a pharmaceutical composition.

15. The antimicrobial composition of claim 1, wherein the targeted antimicrobial protein is in nanomolar concentrations.

16. The antimicrobial composition of claim 1, wherein the antimicrobial composition is in a lyophilized form.

17. An antimicrobial composition comprising
an effective amount of a targeted antimicrobial protein for *Bacillus cereus* or a microorganism related thereto,
polyamines; and
a suitable vehicle,
wherein the targeted antimicrobial protein has a catalytic domain and a binding domain, the targeted antimicrobial protein being BCZK2532 protein having SEQ ID NO: 3 and/or a related lysin protein having lytic activity,
wherein the related lysin protein has at least a 40% percentage identity with the BCZK2532 protein having SEQ ID NO: 3 or a portion thereof, and
wherein the related lysin protein has an arginine in a position corresponding upon alignment to amino acid residue 100 of SEQ ID NO: 3.

18. The antimicrobial composition of claim 17, wherein the antimicrobial composition is in a lyophilized form.

19. The antimicrobial composition of claim 17, wherein the microorganism related thereto comprises *B. anthracis, B. thuringiensis* 97-27, *B. thuringiensis* HD1, *B. thuringiensis* HD560 and *B. thuringiensis* HD658.

20. The antimicrobial composition of claim 17, wherein the portion thereof is the catalytic domain and/or the binding domain of the BCZK2532 protein and wherein the catalytic domain and/or the binding domain of the related lysin protein has at least a 90% identity with the catalytic domain and/or the binding domain of the BCZK2532 protein.

21. The antimicrobial composition of claim 17, wherein the composition comprises an additional one or more antimicrobials.

22. The antimicrobial composition of claim 17, wherein the composition comprises an additional one or more antibiotics.

23. The antimicrobial composition of claim 17, wherein the vehicle is a pharmaceutically acceptable vehicle and the composition is a pharmaceutical composition.

24. An antimicrobial composition comprising
an effective amount of a targeted antimicrobial protein for *Bacillus cereus* or a microorganism related thereto,
a suitable vehicle,
one or more polyamines and/or polymixins,
wherein the targeted antimicrobial protein has a catalytic domain and a binding domain, the targeted antimicrobial protein being BCZK2532 protein having SEQ ID NO:3 and/or a related lysin protein having lytic activity,
wherein the related lysin protein has at least a 40% percentage identity with the BCZK2532 protein having SEQ ID NO:3 or a portion thereof, and
wherein the related lysin protein has an arginine in a position corresponding upon alignment to amino acid residue 100 of SEQ ID NO:3,
the targeted antimicrobial protein further comprising a tag.

25. The antimicrobial composition of claim 24, wherein the antimicrobial composition is in a lyophilized form.

26. The antimicrobial composition of claim 24, wherein the microorganism related thereto comprises *B. anthracis, B. thuringiensis* 97-27, *B. thuringiensis* HD1, *B. thuringiensis* HD560 and *B. thuringiensis* HD658.

27. The antimicrobial composition of claim 24, wherein the portion thereof is the catalytic domain and/or the binding domain of the BCZK2532 protein and wherein the catalytic domain and/or the binding domain of the related lysin protein has at least a 90% identity with the catalytic domain and/or the binding domain of the BCZK2532 protein.

28. The antimicrobial composition of claim 24, wherein the composition comprises one or more additional antimicrobials.

29. The antimicrobial composition of claim 28, wherein the antimicrobial is one or more antibiotics.

30. The antimicrobial composition of claim 24, wherein the vehicle is a pharmaceutically acceptable vehicle and the composition is a pharmaceutical composition.

31. An antimicrobial system comprising:
an effective amount of one or more targeted antimicrobial proteins specific for *Bacillus cereus* or one or more related microorganisms,
one or more polyamines and/or polymixins, and optionally
suitable reagents, and
an additional antimicrobial,
wherein the one or more targeted antimicrobial proteins comprise BCZK2532 protein having a SEQ ID NO: 3 and/or one or more related lysin proteins having lytic activity;
wherein the one or more related lysin proteins have at least a 40% percentage identity with the BCZK2532 protein having SEQ ID NO: 3 or a portion thereof, and
wherein the one or more related lysin proteins have an arginine in a position corresponding upon alignment to amino acid residue 100 of SEQ ID NO: 3.

32. An antimicrobial system comprising:
an effective amount of a targeted antimicrobial protein specific for *Bacillus cereus* or one or more related microorganisms;
polyamines;
suitable reagents, and
an additional antimicrobial,
wherein the targeted antimicrobial protein comprises BCZK2532 protein having a SEQ ID NO: 3 and/or one or more related lysin protein having lytic activity,
wherein the related lysin protein has at least a 40% percentage identity with the BCZK2532 protein having SEQ ID NO: 3 or a portion thereof, and
wherein the related lysin protein has an arginine in a position corresponding upon alignment to amino acid residue 100 of SEQ ID NO: 3.

33. An antimicrobial system comprising:
an effective amount of a targeted antimicrobial protein specific for *Bacillus cereus* or one or more related microorganisms, the one or more targeted antimicrobial protein comprising BCZK2532 protein having a SEQ ID NO: 3 and/or one or more a related lysin protein having lytic activity;
one or more polyamines and/or polymixins,
one or more antibiotics, and
optionally suitable reagents,
wherein the one or more related lysin protein has at least a 90% percentage identity with the BCZK2532 protein having SEQ ID NO: 3 or a portion thereof, and
wherein the one or more related lysin protein has an arginine in a position corresponding upon alignment to amino acid residue 100 of SEQ ID NO: 3,
the targeted antimicrobial protein further comprising a tag.

34. An antimicrobial method comprising
contacting a targeted antimicrobial BCZK2532 protein having SEQ ID NO: 3 and/or one or more related lysin proteins having lytic activity with a medium suitable to host *Bacillus cereus* or one or more related microorganisms, the contacting performed for a time and under condition to specifically kill or inhibit the growth of the one or more related microorganisms if present in the medium
wherein the one or more related lysin proteins have at least a 40% percentage identity with the BCZK2532 protein having SEQ ID NO:3 or a portion thereof, and
wherein the one or more related lysin proteins have an arginine in a position corresponding upon alignment to amino acid residue 100 of SEQ ID NO:3.

35. The antimicrobial method of claim 34, wherein the medium is a solid and/or fluidic medium.

36. The antimicrobial method of claim 34, wherein the one or more related microorganisms comprises *B. anthracis, B. thuringiensis* 97-27, *B. thuringiensis* HD1, *B. thuringiensis* HD560 and *B. thuringiensis* HD658.

37. The antimicrobial method of claim 34, wherein the targeted antimicrobial BCZK2532 protein having SEQ ID NO:3 and/or one or more related lysin proteins having lytic activity is in combination with an additional antimicrobial.

38. An antimicrobial method, comprising:
administering to an individual in a therapeutically effective amount of a targeted antimicrobial BCZK2532 protein having a SEQ ID NO: 3 and/or one or more related lysin proteins having lytic activity to treat or prevent a condition associated with *Bacillus cereus* or one or more related microorganisms in the individual,
wherein the one or more related lysin proteins have at least a 40% percentage identity with the BCZK2532 protein having SEQ ID NO: 3 or a portion thereof, and
wherein the one or more related lysin proteins have an arginine in a position corresponding upon alignment to amino acid residue 100 of SEQ ID NO: 3.

39. The antimicrobial method of claim 38, wherein the one or more related microorganisms comprises *B. anthracis, B. thuringiensis* 97-27, *B. thuringiensis* HD1, *B. thuringiensis* HD560 and *B. thuringiensis* HD658.

40. The antimicrobial method of claim 38, wherein the targeted antimicrobial BCZK2532 protein having SEQ ID NO: 3 and/or one or more related lysin proteins having lytic activity is in combination with an additional antimicrobial.

* * * * *

SEQUENCE LISTING

<160> NUMBER OF SEQ ID NOS: 7

<210> SEQ ID NO 1
<211> LENGTH: 234
<212> TYPE: PRT
<213> ORGANISM: Bacillus anthracis -continued

```
<400> SEQUENCE: 1

Met Glu Ile Arg Lys Lys Leu Val Val Pro Ser Lys Tyr Gly Thr Lys
1               5                   10                  15

Cys Pro Tyr Thr Met Lys Pro Lys Tyr Ile Thr Val His Asn Thr Tyr
                20                  25                  30

Asn Asp Ala Pro Ala Glu Asn Glu Val Asn Tyr Met Ile Thr Asn Asn
            35                  40                  45

Asn Glu Val Ser Phe His Val Ala Val Asp Asp Lys Gln Ala Ile Gln
50                  55                  60

Gly Ile Pro Trp Glu Arg Asn Ala Trp Ala Cys Gly Asp Gly Asn Gly
65                  70                  75                  80

Pro Gly Asn Arg Glu Ser Ile Ser Val Glu Ile Cys Tyr Ser Lys Ser
                85                  90                  95

Gly Gly Asp Arg Tyr Tyr Lys Ala Glu Asn Asn Ala Val Asp Val Val
                100                 105                 110

Arg Gln Leu Met Ser Met Tyr Asn Ile Pro Ile Glu Asn Val Arg Thr
            115                 120                 125

His Gln Ser Trp Ser Gly Lys Tyr Cys Pro His Arg Met Leu Ala Glu
130                 135                 140

Gly Arg Trp Gly Ala Phe Ile Gln Lys Val Lys Ser Gly Asn Val Ala
145                 150                 155                 160

Ser Ala Thr Val Thr Pro Lys Gln Asn Ile Ile Gln Thr Gly Ala Phe
                165                 170                 175

Ser Pro Tyr Glu Leu Pro Asp Ala Val Gly Ala Leu Lys Ser Leu Asn
            180                 185                 190

Met Thr Gly Lys Ala Ile Ile Asn Pro Glu Gly Leu Thr Tyr Ile Val
        195                 200                 205

Thr Asp Pro Thr Ser Asp Val Gln Leu Gln Ala Phe Lys Glu Tyr Leu
210                 215                 220

Glu Arg Lys Asp Trp Trp Tyr Asp Asp Lys
225                 230

<210> SEQ ID NO 2
<211> LENGTH: 263
<212> TYPE: PRT
<213> ORGANISM: Bacteriophage TP21-T

<400> SEQUENCE: 2

Met Gln Ile Lys Gln Met Leu Val Pro Glu Tyr Lys Tyr Glu Leu Leu
1               5                   10                  15

Cys Pro Asn Pro Met Thr Pro Thr Glu Ile Thr Leu His Asn Thr Tyr
                20                  25                  30

Asn Asp Ala Pro Ala Ile Asn Glu Arg Asn Asn Val Ala Asn Asn Ser
            35                  40                  45

Gln Gly Thr Ser Phe His Val Val Asp Asp Lys Glu Ala Ile Gln
50                  55                  60

Leu Ile Pro Phe Asn Arg Asn Ala Trp His Ala Gly Asp Gly Gly Ser
65                  70                  75                  80

Gly Arg Gly Asn Arg His Ser Ile Gly Val Glu Ile Cys Tyr Ser Lys
                85                  90                  95

Ser Gly Gly Pro Arg Tyr Glu Gln Ala Val Arg Asn Ala Ile Ile Val
            100                 105                 110

Ile Arg Gln Leu Met Asp Gln Phe Asn Ile Pro Ile Asp Arg Val Lys
        115                 120                 125
```

```
Thr His Gln Glu Arg Asn Gly Lys Tyr Cys Pro His Arg Met Leu Ala
        130                 135                 140
Glu Gly Arg Val Gly Trp Phe Lys Gln Gln Leu Val Ser Gly Asp Tyr
145                 150                 155                 160
Val Pro Pro Thr Pro Ile Pro Gln Pro Glu Pro Gln Leu Pro Ser Gly
                165                 170                 175
Gln Tyr Asp Ser Ser Trp Phe Thr Lys Glu Ser Gly Thr Phe Thr Leu
                180                 185                 190
Asn Thr Thr Ile Asn Leu Arg Thr Ala Pro Phe Ser Asn Ala Pro Leu
                195                 200                 205
Ile Ala Thr Leu Ser Lys Gly Gln Gln Val Ser Tyr Asp Gly Tyr Gly
                210                 215                 220
Ile Glu Leu Asp Gly His Val Trp Ile Arg Gln Pro Arg Ala Asn Gly
225                 230                 235                 240
Thr Tyr Gly Tyr Met Ala Thr Gly Glu Ser Ala Asn Gly Lys Arg Val
                245                 250                 255
Asp Tyr Trp Gly Ser Phe Lys
                260

<210> SEQ ID NO 3
<211> LENGTH: 268
<212> TYPE: PRT
<213> ORGANISM: Bacillus cereus E33L

<400> SEQUENCE: 3

Met Gly Tyr Ile Val Asp Ile Ser Lys Trp Asn Gly Asn Ile Asn Trp
1               5                   10                  15
Asp Val Ala Ala Pro Gln Leu Asp Phe Val Ile Ala Arg Val Gln Asp
                20                  25                  30
Gly Ser Asn Tyr Ile Asp Pro Leu Tyr Lys Ser Tyr Val Gln Ala Met
                35                  40                  45
Lys Thr Arg Asn Ile Pro Phe Gly Asn Tyr Ala Phe Cys Arg Phe Ile
    50                  55                  60
Ser Ile Ala Asp Ala Lys Lys Glu Ala Gln Asp Phe Trp Asn Arg Gly
65                  70                  75                  80
Asp Lys Ser Ala Thr Val Trp Val Ala Asp Val Glu Val Lys Thr Met
                85                  90                  95
Asp Asp Met Arg Ala Gly Thr Gln Ala Phe Ile Asp Glu Leu Arg Arg
                100                 105                 110
Leu Gly Ala Lys Lys Val Gly Leu Tyr Val Gly His His Met Tyr Gly
                115                 120                 125
Pro Phe Gly Met Ala Asn Val Lys Ser Asp Phe Val Trp Ile Pro Arg
        130                 135                 140
Tyr Gly Gly Asn Lys Pro Ala Tyr Pro Cys Asp Ile Trp Gln Tyr Thr
145                 150                 155                 160
Glu Thr Gly Asn Val Pro Gly Ile Gly Lys Cys Asp Leu Asn Gln Leu
                165                 170                 175
Ile Gly Asn Lys Pro Leu Ser Trp Phe Thr Glu Ser Val Pro Lys Gln
                180                 185                 190
Glu Asn Ile Gln Ala Gln Val Ser Lys Gln Asn Ile Ile Gln Ser Gly
                195                 200                 205
Ala Phe Ser Pro Tyr Glu Thr Pro Asp Val Met Gly Ala Leu Thr Ser
                210                 215                 220
Leu Lys Met Thr Ala Thr Phe Ile Leu Gln Ser Asp Gly Leu Thr Tyr
```

```
225                 230                 235                 240
Phe Val Thr Glu Pro Thr Ser Asp Thr Gln Leu Asn Ala Leu Lys Ser
                245                 250                 255
Trp Leu Asp Arg Lys Gly Trp Trp Tyr Glu Val Lys
                260                 265
```

<210> SEQ ID NO 4
<211> LENGTH: 268
<212> TYPE: PRT
<213> ORGANISM: B. anthracis

<400> SEQUENCE: 4

```
Met Gly Tyr Ile Val Asp Ile Ser Lys Trp Asn Gly Asn Ile Asn Trp
1               5                   10                  15
Asp Val Ala Ala Pro Gln Leu Asp Phe Val Ile Ala Arg Val Gln Asp
                20                  25                  30
Gly Ser Asn Tyr Ile Asp Pro Leu Tyr Lys Ser Tyr Val Gln Ala Met
                35                  40                  45
Lys Thr Arg Asn Ile Pro Phe Gly Asn Tyr Ala Phe Cys Arg Phe Ile
            50                  55                  60
Ser Ile Ala Asp Ala Lys Lys Glu Ala Gln Asp Phe Trp Asn Arg Gly
65                  70                  75                  80
Asp Lys Ser Ala Thr Val Trp Val Ala Asp Val Glu Val Lys Thr Met
                85                  90                  95
Asp Asp Met Ile Ala Gly Thr Gln Ala Phe Ile Asp Glu Leu Arg Arg
            100                 105                 110
Leu Gly Ala Lys Lys Val Gly Leu Tyr Val Gly His His Met Tyr Gly
            115                 120                 125
Pro Phe Gly Met Ala Asn Val Lys Ser Asp Phe Val Trp Ile Pro Arg
        130                 135                 140
Tyr Gly Gly Asn Lys Pro Ala Tyr Pro Cys Asp Ile Trp Gln Tyr Thr
145                 150                 155                 160
Glu Thr Gly Asn Val Pro Gly Ile Gly Lys Cys Asp Leu Asn Gln Leu
                165                 170                 175
Ile Gly Asn Lys Pro Leu Ser Trp Phe Thr Glu Ser Val Pro Lys Gln
            180                 185                 190
Glu Asn Ile Gln Ala Gln Val Ser Lys Gln Asn Ile Ile Gln Ser Gly
            195                 200                 205
Ala Phe Ser Pro Tyr Glu Thr Pro Asp Val Met Gly Ala Leu Thr Ser
        210                 215                 220
Leu Lys Met Thr Ala Thr Phe Ile Leu Gln Ser Asp Gly Leu Thr Tyr
225                 230                 235                 240
Phe Val Thr Glu Pro Thr Ser Asp Thr Gln Leu Asn Ala Leu Lys Ser
                245                 250                 255
Trp Leu Asp Arg Lys Gly Trp Trp Tyr Glu Val Lys
                260                 265
```

<210> SEQ ID NO 5
<211> LENGTH: 245
<212> TYPE: PRT
<213> ORGANISM: B. anthracis

<400> SEQUENCE: 5

```
Met Ala Arg Tyr Ser Leu His Ala Gly His Asn Ser Ile Val Gln Gly
1               5                   10                  15
Ala Asn Tyr Gly Asn Arg Lys Glu His Ile Met Asp Arg Gln Val Lys
```

```
                    20                  25                  30
Asp Ala Val Ala Lys Leu Arg Ala Leu Gly His Thr Val Tyr Asp
            35                  40                  45
Asp Thr Asp Glu Val Gly Thr Thr Gln Ala Gln Asn Leu Asn Asn Ile
        50                  55                  60
Val Ser Lys Thr Asn Ser His Asp Val Asp Leu Val Val Ser Phe His
65                  70                  75                  80
Leu Asn Ser Tyr Asp Thr Arg Ala Asn Gly Val Glu Val Leu Tyr Tyr
                85                  90                  95
Asp Gln Gln Ala Leu Ser Ala Lys Ile Ala Ala Gln Leu Ser Lys Asp
            100                 105                 110
Ile Gly Trp Ser Asn Arg Gly Ala Lys Glu Arg Lys Asp Leu Tyr Val
            115                 120                 125
Leu Ser Asn Thr Lys Ala Pro Ala Ile Leu Ile Glu Leu Gly Phe Ile
            130                 135                 140
Asp Asn Glu Ala Asp Met Ala Lys Trp Asn Pro Asp Lys Ile Ala Asn
145                 150                 155                 160
Ser Ile Val Tyr Ala Leu Thr Gly Gln Ser Gly Gly Thr Thr Pro Pro
                165                 170                 175
Ser Lys Gln Asn Ile Ile Gln Ser Gly Ala Phe Ser Pro Tyr Glu Thr
                180                 185                 190
Pro Asp Val Met Gly Ala Leu Thr Ser Leu Lys Met Thr Ala Asn Phe
            195                 200                 205
Ile Leu Gln Ser Asp Gly Leu Thr Tyr Phe Ile Ser Glu Pro Thr Ser
        210                 215                 220
Asp Ala Gln Leu Lys Gly Met Thr Asp Tyr Leu Asp Arg Arg Gly Trp
225                 230                 235                 240

Trp Tyr Glu Val Lys
            245

<210> SEQ ID NO 6
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 6
ggccatgggg catatgggtt atattgtaga tatttcg                              37

<210> SEQ ID NO 7
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 7
cccccgggat cctttaactt cataccacca ac                                   32
```